United States Patent
Wolf et al.

(10) Patent No.: US 9,883,847 B2
(45) Date of Patent: Feb. 6, 2018

(54) ULTRASOUND LOCALIZATION OF OBSTRUCTION FOR OBSTRUCTIVE SLEEP APNEA

(71) Applicant: University of Maryland, Baltimore, Baltimore, MD (US)

(72) Inventors: Jeffrey S. Wolf, Owings Mills, MD (US); Amal Isaiah, Elicott City, MD (US)

(73) Assignee: University Of Maryland, Baltimore, Baltimore, MD (US)

( * ) Notice: Subject to any disclaimer, the term of this patent is extended or adjusted under 35 U.S.C. 154(b) by 241 days.

(21) Appl. No.: 14/608,859

(22) Filed: Jan. 29, 2015

(65) Prior Publication Data
US 2015/0209001 A1 Jul. 30, 2015

Related U.S. Application Data

(60) Provisional application No. 61/932,845, filed on Jan. 29, 2014.

(51) Int. Cl.
*A61B 8/08* (2006.01)
*A61B 8/00* (2006.01)
(Continued)

(52) U.S. Cl.
CPC .............. *A61B 8/085* (2013.01); *A61B 7/003* (2013.01); *A61B 8/0858* (2013.01); *A61B 8/145* (2013.01);
(Continued)

(58) Field of Classification Search
CPC .. A61B 8/08; A61B 8/00; A61B 8/422; A61B 8/445
(Continued)

(56) References Cited

U.S. PATENT DOCUMENTS 5,181,513 A * 1/1993 Touboul ............. A61B 5/02007
600/443
2006/0173348 A1 8/2006 Wilser et al.
(Continued)

OTHER PUBLICATIONS

ISA/US, "International Search Report and Written Opinion for the corresponding PCT application 2015/013549", dated May 7, 2015.
(Continued)

*Primary Examiner* — Carl H Layno
*Assistant Examiner* — Jon Eric C Morales
(74) *Attorney, Agent, or Firm* — Eugene J. Molinelli; Beusse Wolter Sanks & Maire

(57) ABSTRACT

Techniques for ultrasound location of obstructions during OSA include an ultrasound transducer array configured, upon receipt of a signal, to obtain first data that supports a plurality of ultrasound images representing a corresponding plurality of cross sections of an airway in a neck of a subject. Second data is received automatically on a processor, from an apnea event sensor set that is configured to collect automatically the second data sensitive to an apnea event in the subject. An apnea event is detected automatically on the processor based on the second data. In response to detecting the apnea event, the signal is automatically sent to the ultrasound transducer array, wherein the signal is the signal that causes the ultrasound transducer array to obtain the first data. Image data based on the first data is automatically stored in a computer-readable medium.

16 Claims, 19 Drawing Sheets

(51) Int. Cl.
| | |
|---|---|
| *A61B 5/113* | (2006.01) |
| *A61B 8/14* | (2006.01) |
| *A61B 7/00* | (2006.01) |
| *A61B 8/15* | (2006.01) |
| *A61B 5/00* | (2006.01) |

(52) U.S. Cl.
CPC .............. *A61B 8/15* (2013.01); *A61B 8/5223* (2013.01); *A61B 5/4818* (2013.01); *A61B 8/4227* (2013.01); *A61B 8/4461* (2013.01); *A61B 8/4494* (2013.01); *A61B 8/543* (2013.01); *A61B 8/56* (2013.01)

(58) Field of Classification Search
USPC .................................................. 600/442, 443
See application file for complete search history.

(56) References Cited

U.S. PATENT DOCUMENTS

| | | | |
|---|---|---|---|
| 2007/0078345 | A1 | 4/2007 | Mo et al. |
| 2012/0022365 | A1 | 1/2012 | Mansfield |
| 2012/0095343 | A1 | 4/2012 | Smith et al. |
| 2013/0030257 | A1 | 1/2013 | Nakata et al. |
| 2013/0144190 | A1 | 1/2013 | Bruce et al. |
| 2013/0046181 | A1 | 2/2013 | Al-Abed et al. |
| 2013/0289401 | A1* | 10/2013 | Colbaugh ............ A61B 5/0488 600/437 |
| 2013/2289401 | | 10/2013 | Colbaugh et al. |

OTHER PUBLICATIONS

Collop, N., et al., "Clinical guidelines for the use of unattended portable monitors in the diagnosis of obstructive sleep apnea in adult patients", "J Clin Sleep Med", 2007, pp. 737-747, vol. 3, No. 7, Publisher: American Academy of Sleep Medicine, Published in: http://www.aasmnet.org/jcsm/ViewAbstract.aspx?pid=27032.

Ezri, T., et al., "Prediction of difficult laryngoscopy in obese patients by ultrasound quantification of anterior neck soft tissue", "Anaesthesia", 2003, pp. 1111-1114, vol. 58, Publisher: Association of Anaesthetists of Great Britain and Ireland, Published in: http://onlinelibrary.wiley.com/doi/10.1046/j.1365-2044.2003.03412.x/pdf.

Girard, Erin Elizabeth, "Automated Detection of Obstructive Sleep Apnea Using Ultrasound Imaging", "Thesis in partial fulfillment of the requirements for the degree Master of Science in Biomedical Engineering", 2003, pp. 1-79, Publisher: University of Virginia, Published in: Charlottesville, VA.

Kajekar, P., et al., "Role of Ultrasound in Airway Assessment and Management", "International J Ultrasound & Applied Technologies in Perioperative Care", 2010, pp. 97-100, vol. 1, No. 2, Publisher: Society for Ultrasound in Anaesthesia, Published in: http://jaypeejournals.com/eJournals/TopicDetails.aspx?id=80&AID=14.

Riley, R. W., et al., "Obstructive sleep apnea syndrome: a review of 306 consecutively treated surgical patients", "Otolaryngology—Head and Neck Surgery", 1993, pp. 117-125, vol. 108, No. 2, Publisher: American Academy of Otolaryngology—Head and Neck Surgery Foundation, Published in: http://oto.sagepub.com/content/108/2/117.full.pdf+html.

Siegel, H., et al., "Obstructive sleep apnea: A study by simultaneous polysomnography and ultrasonic imaging", "Neurology", 2000, p. 1872 vol. 54, Publisher: American Academy of Neurology, Published in: http://www.neurology.org/content/54/9/1872.full.pdf+html?sid=41864db2-5400-40af-82c0-efcd9ad924c1.

Veasey, S. C., et al., "Medical therapy for obstructive sleep apnea: a review by the Medical Therapy for Obstructive Sleep Apnea Task Force of the Standards of Practice Committee of the American Academy of Sleep Medicine", "Sleep", 2006, p. 1036 vol. 29, No. 8, Publisher: Associated Professional Sleep Societies, Published in: http://www.journalsleep.org/ViewAbstract.aspx?pid=26612.

Shu, Chin-Chung et al., "The Use of Sub-Mental Ultrasonography for Identifying Patients with Severe Obstructive Sleep Apnea," PLOS One, Published May 10, 2013, vol. 8, Issue 5, pp. 1-7.†

* cited by examiner
† cited by third party

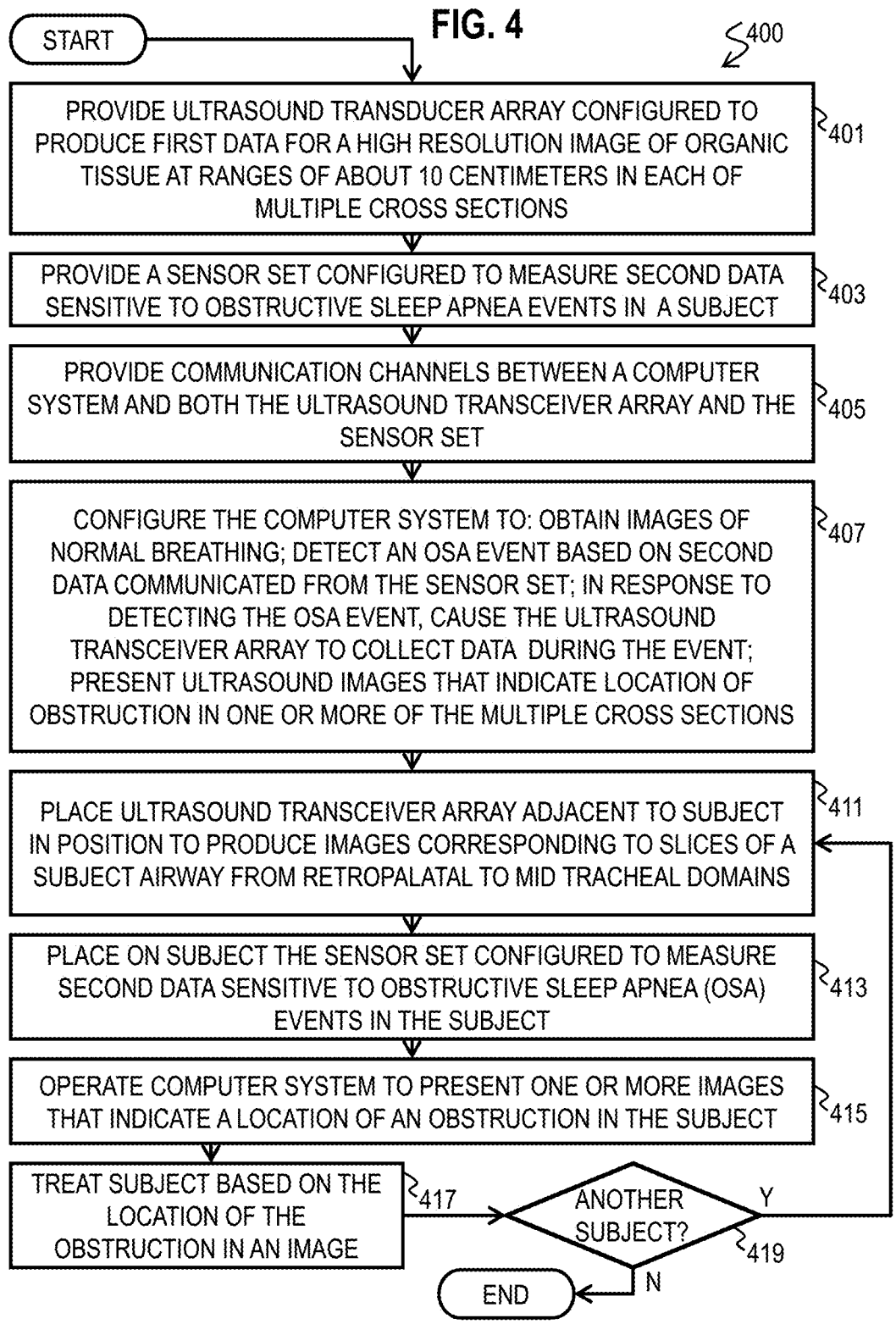

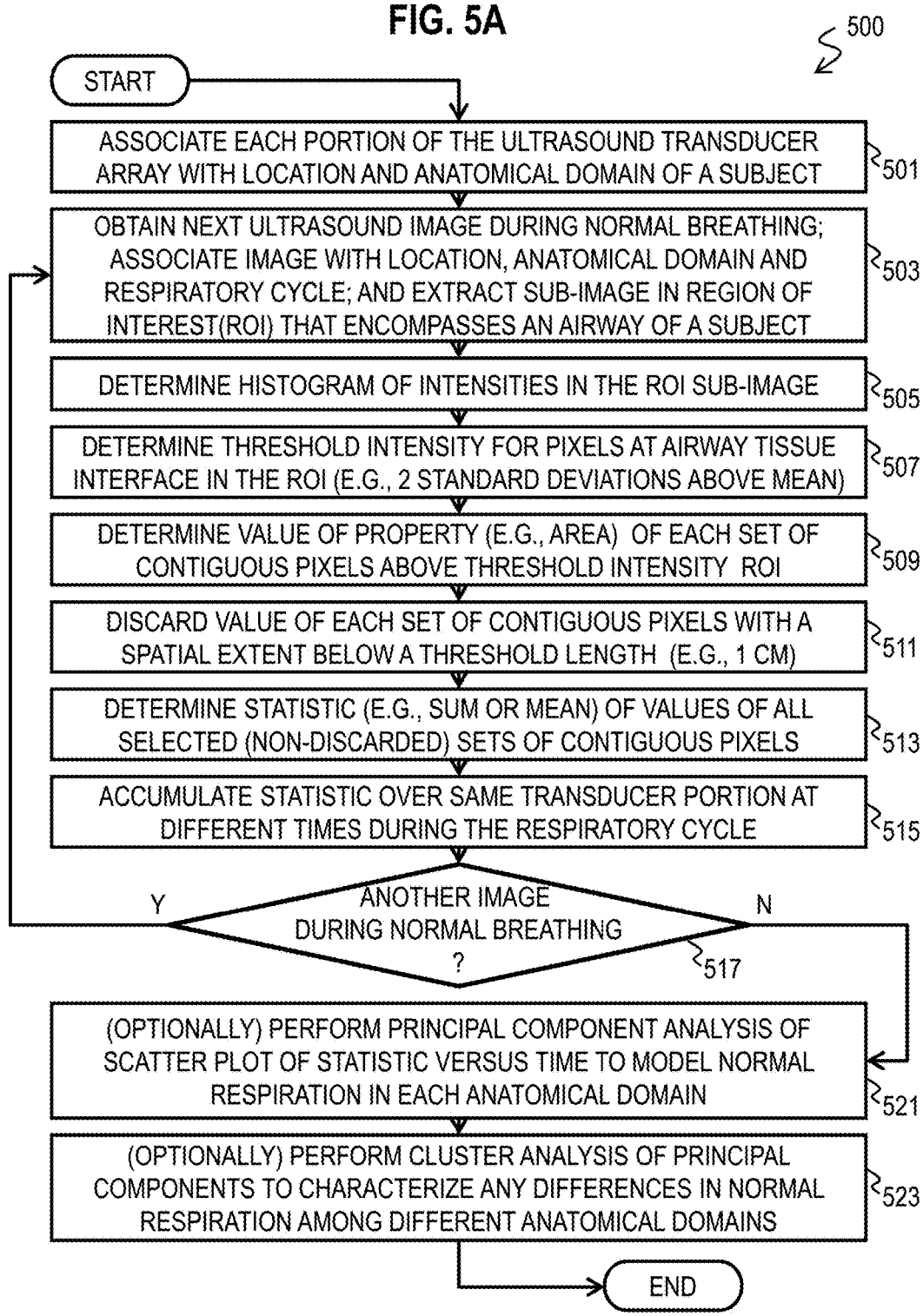

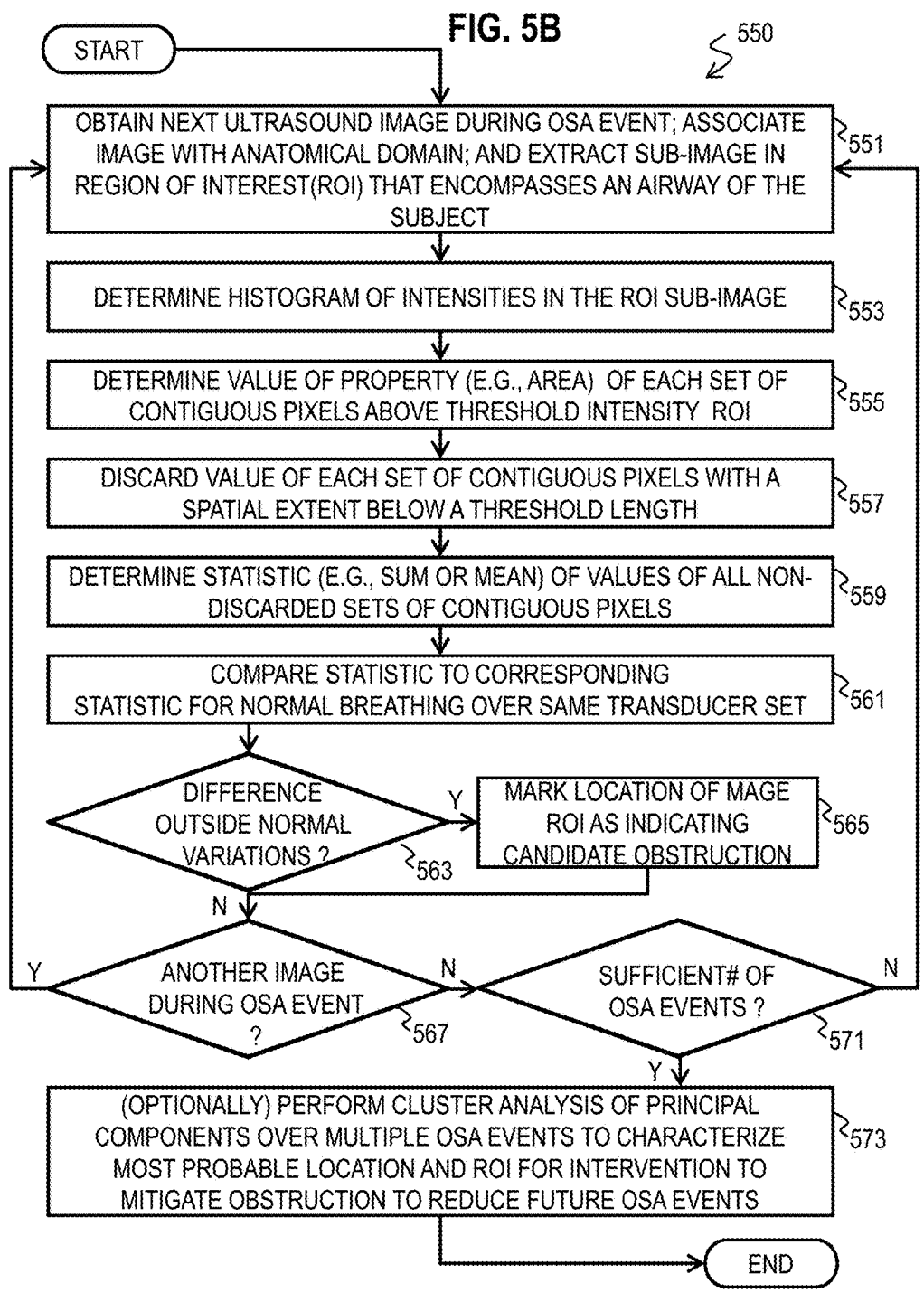

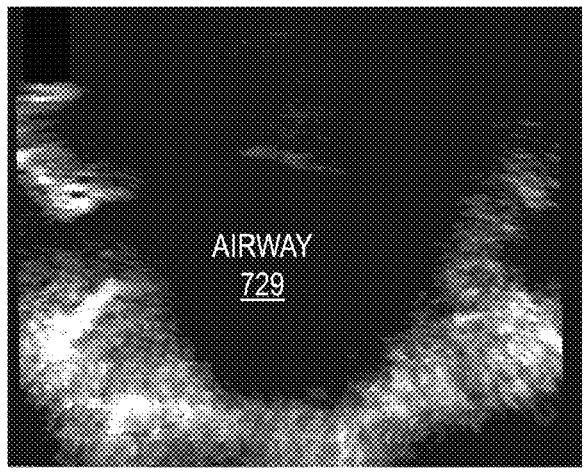
FIG. 7A — RETROPALATAL ROI 720 — AIRWAY 729
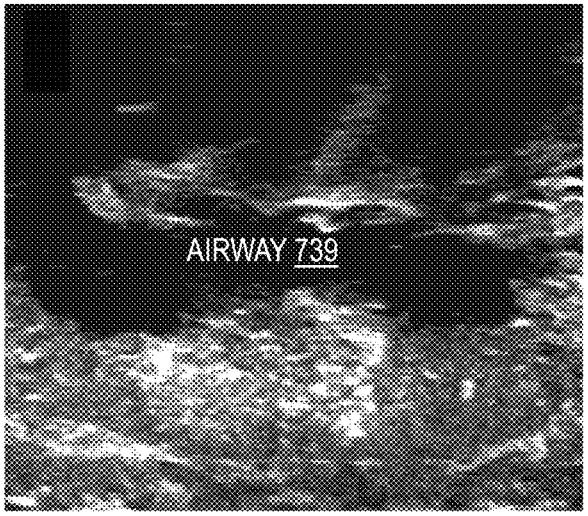
FIG. 7B — RETROLINGUAL ROI 730 — AIRWAY 739
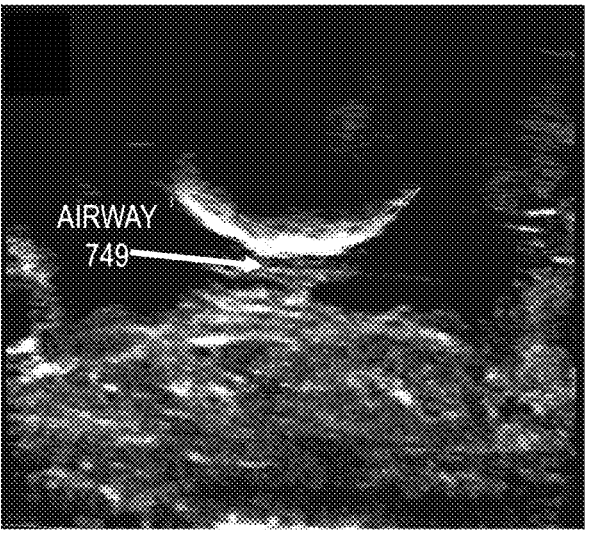
FIG. 7C — HYPOPHARYNGEAL ROI 740 — AIRWAY 749

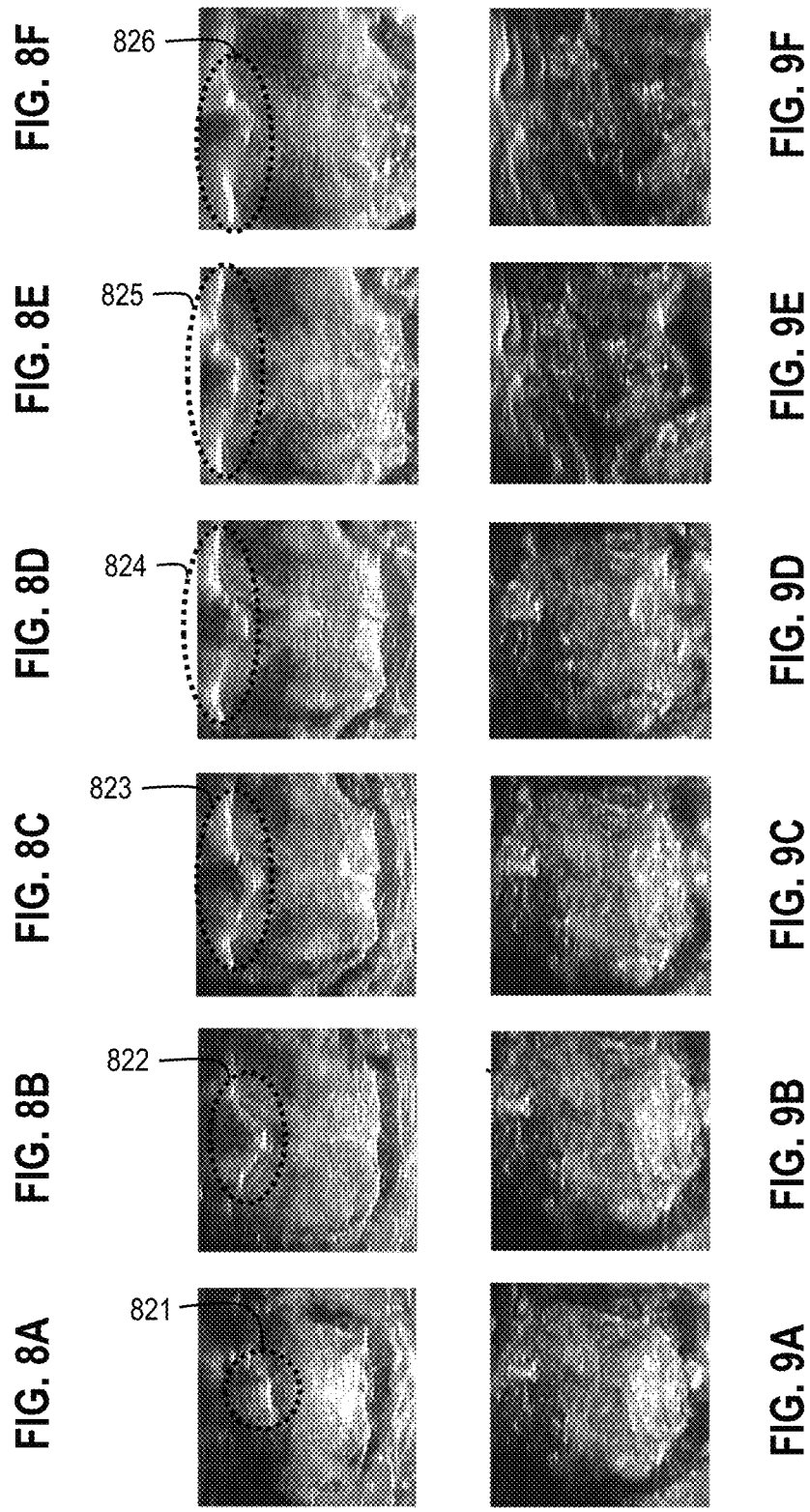

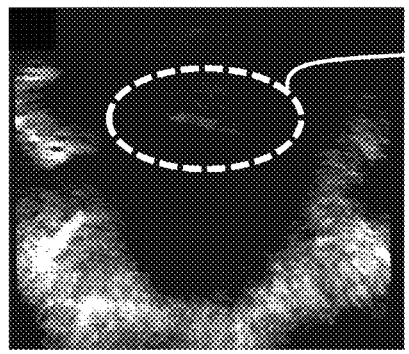
FIG. 10A — BACK OF AIRWAY 1010a
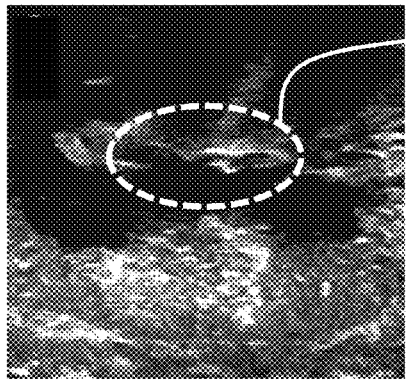
FIG. 10B — BACK OF AIRWAY 1010b
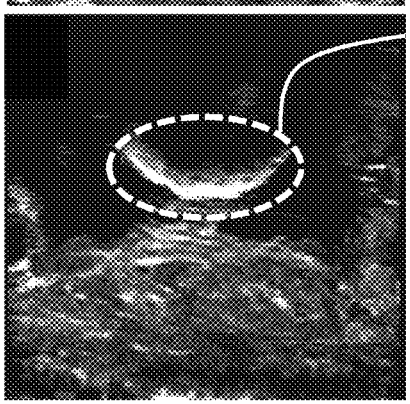
FIG. 10C — BACK OF AIRWAY 1010c BACK OF AIRWAY
1110a BACK OF AIRWAY
1110b

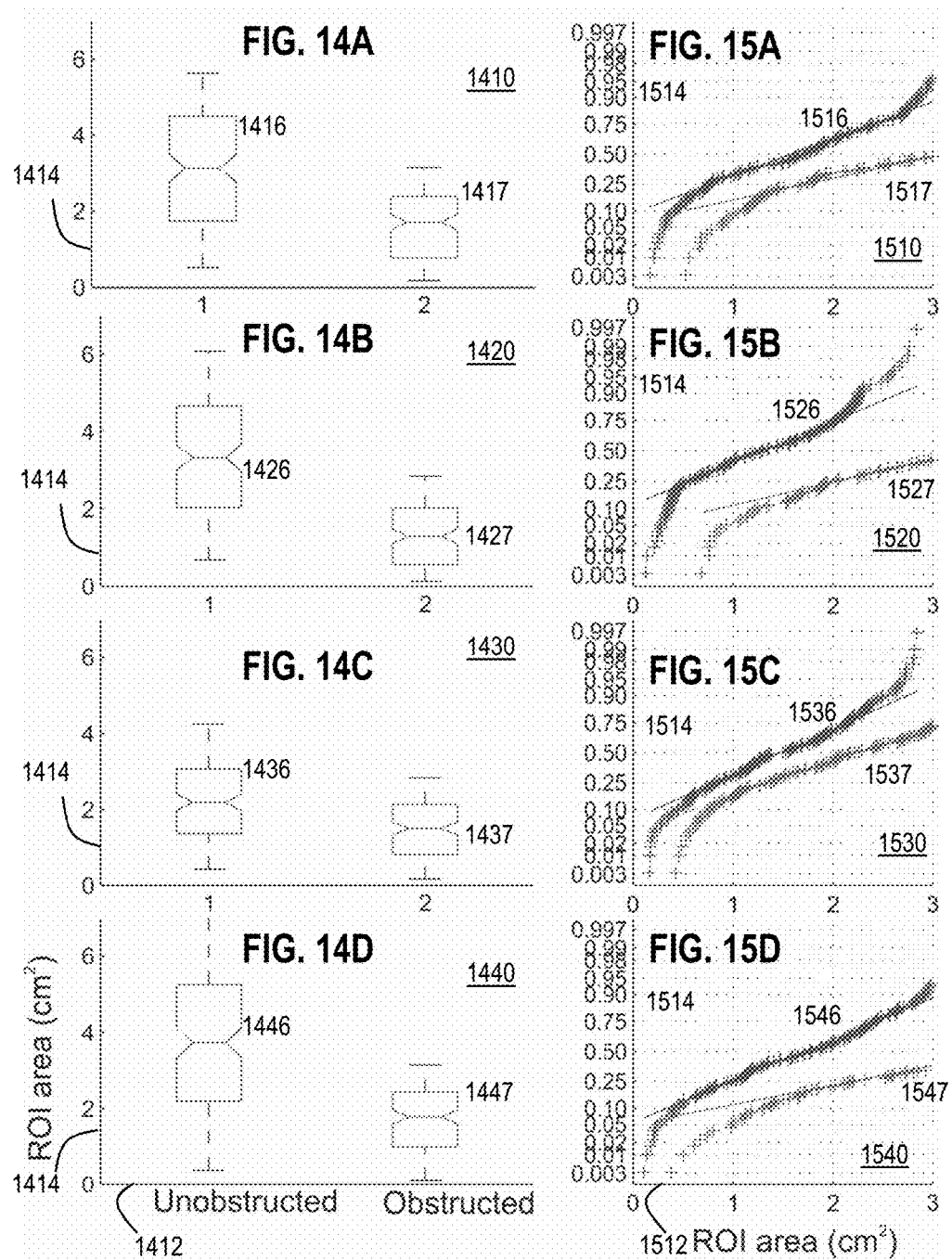

Array of probes

ULTRASOUND TRANSDUCER ARRAY 1612

Unsupervised classification

GRAPHS 1650

Behind the palate

Behind the tongue

Separation boundary

COMPOSITE GRAPH 1660

ULTRASOUND LOCALIZATION OF OBSTRUCTION FOR OBSTRUCTIVE SLEEP APNEA

CROSS-REFERENCE TO RELATED APPLICATIONS

This application claims benefit of Provisional Appln. 61/932,845, filed Jan. 29, 2014, the entire contents of which are hereby incorporated by reference as if fully set forth herein, under 35 U.S.C. §119(e).

STATEMENT OF GOVERNMENT INTEREST

This work was supported by the U.S. Department of Veterans Affairs, and the federal government has certain rights in this invention.

BACKGROUND

Obstructive sleep apnea (OSA) syndrome occurs with an estimated prevalence of 2-9% in adult American population with an increasing incidence (Strollo et al. 1996; Shamsuzzaman et al. 2003). OSA has been recognized as a major cause of morbidity in recent years. The condition is firmly seated within a spectrum of sleep-related breathing disorders (Flemons 2002), including snoring, upper airway resistance syndrome and obesity-hypoventilation syndrome. Left untreated, OSA can manifest in conditions with significant detriment to quality of life: daytime sleepiness (Johns 1993) and cognitive impairment (Findley et al. 1986). More significantly untreated OSA leads to increased morbidity and mortality from systemic and pulmonary hypertension (Marin et al. 2005), myocardial infarction (Hung et al. 1993), cardiac arrhythmias (Guilleminault et al. 1983), stroke and an increased risk of motor vehicle accidents (Teran-Santos et al. 1999). Given these implications, accurate and early diagnosis of OSA can potentially benefit early interventions to halt initiation and progression of cardiovascular diseases. However, due to the lack of consensus regarding specific diagnostic tools and criteria, most of the patients with OSA remain untreated and the management of complications adds to the burden of healthcare costs.

Obstructive events occur when tissue in the upper airway collapses during sleep. This occurs during the negative pressure environment of inspiration. The exact sites of collapse vary in each person depending on their anatomy and to date there is no acceptable mechanism to predict or identify site of obstruction.

SUMMARY

Techniques are provided for the automatic collection of ultrasound imaging data for localization of an obstruction contributing to obstructive sleep apnea. Ultrasound is defined as pressure waves in a medium at frequencies higher than those detectable by normal human auditory systems, and includes frequencies from about 20 kilohertz (kHz, 1 kHz=$10^3$ Hertz, 1 Hertz, Hz, is one cycle per second) up to about several gigahertz (GHz, 1 GHz=$10^9$ Hertz). For use in non-invasive imaging of human tissues to practical depths of tens of centimeters (cm, 1 cm=$10^{-2}$ meters) ultrasound frequencies in the range from about 2 to 100 megahertz (MHz, 1 MHz=$10^6$ Hertz) are used. To avoid heating and destructive effects, the power area density of such ultrasound waves is less than about 1 watt per square centimeter ($Wcm^{-2}$).

In a first set of embodiments, a method includes placing an ultrasound transducer array such that the ultrasound transducer array is adjacent to a neck of a subject. The transducer array is configured, upon receipt of a signal, to obtain first data that supports a plurality of ultrasound images representing a corresponding plurality of cross sections of an airway in the neck of the subject. The method also includes receiving, automatically on a processor, second data from an apnea event sensor set that is configured to collect automatically the second data. The second data is sensitive to an apnea event in the subject. The method still further includes automatically detecting on the processor an apnea event based on the second data. Still further, the method includes, in response to detecting the apnea event, automatically sending, to the ultrasound transducer array, the signal that causes the ultrasound transducer array to obtain the first data. Even further, the method includes automatically causing image data based on the first data to be stored in a computer-readable medium.

In some embodiments of the first set, the apnea sensor set includes one or more sensors from a group including a blood oxygen saturation sensor and a chest movement sensor and a microphone. In some embodiments of the first set, the ultrasound transducer array is removably attached to the subject by an attachment structure.

In some embodiments of the first set, the method also includes automatically determining, on the processor, a location of an obstruction in an airway of the subject based on the first data.

In a second set of embodiments, a system includes an ultrasound transducer array configured, when disposed adjacent to a neck of a subject, to obtain first data upon receipt of a signal. The first data supports a plurality of ultrasound images representing a corresponding plurality of cross sections of an airway in the subject. The system also includes an apnea event sensor set configured to collect automatically second data sensitive to an apnea event in the subject. The system also includes at least one processor and at least one computer-readable medium including one or more sequences of instructions. The at least one memory and the one or more sequences of instructions are configured, with the at least one processor, to cause the system to perform at least the following step. One step is to establish communications with the ultrasound transducer array. Another step is to establish communications with the apnea event sensor set. Another step is to receive the second data. Another step is to detect an apnea event based on the second data. Another step is, in response to detecting the apnea event, to cause the signal that causes the ultrasound transducer array to obtain the first data to be sent to the ultrasound transducer array, and to cause image data based on the first data to be stored in a second computer-readable medium.

In a third set of embodiments, a method includes automatically receiving a first plurality of ultrasound images representing a corresponding plurality of cross sections of an airway in a neck of a subject obtained by an ultrasound transducer array directed toward the subject when the subject has an open airway. The method also includes automatically associating each image in the first plurality of images with a corresponding subset of transducers in the ultrasound transducer array and a location of the corresponding cross section in the subject. The method also includes determining a region of interest made up of a subset of pixels of each image of the first plurality of ultrasound images. Each region of interest encompasses the open airway for each corresponding subset of transducers. The method also includes automatically determining a first value of a statistic of pixel intensities for each region of interest in the first plurality of ultrasound images. The method still further includes automatically receiving a second plurality of ultrasound images representing the corresponding plurality of cross sections of the airway in the neck of the subject obtained by the ultrasound transducer array directed toward the subject when the subject has an obstructive sleep apnea event. Yet further, the method includes automatically determining a second value of the statistic of pixel intensities for each subset of pixels in the second plurality of images that correspond to each region of interest of each image of the first plurality of ultrasound images. Even further, the method includes automatically determining whether the second value is significantly different from the first value for region of interest associated with a particular subset of transducers. If it is determined that the second value is significantly different, then the method includes automatically determining that the region of interest associated with the particular subset of transducers corresponds to a location of an obstruction in the subject during the obstructive sleep apnea event.

In another set of embodiments, a system or a non-transitory computer-readable medium is configured to perform one or more steps of at least one of the above methods.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings, in which like reference numerals refer to similar elements and in which:

FIG. 4 is a flow diagram that illustrates an example method for automatic ultrasound imaging of a subject for determination of location of an obstruction that could contribute to obstructive sleep apnea (OSA), according to an embodiment;

FIG. 5A and FIG. 5B are flow diagrams that illustrates example methods for automatic determination of location of an obstruction in ultrasound images, according to an embodiment;

FIG. 7A through FIG. 7C are labeled photographs that illustrate example regions of interest of images that represent three cross sections of an airway of a subject based on data collected from the rotating 1D array of ultrasound transducers, according to some embodiments;

FIG. 8A through FIG. 8F are labeled photographs that illustrate example regions of interest of images that represent six cross sections for an unobstructed airway of a subject based on data collected from the rotating 1D array of ultrasound transducers, according to some embodiments;

FIG. 9A through FIG. 9F are labeled photographs that illustrate example regions of interest of images that represent the same six cross sections for an obstructed airway of the same subject based on data collected from the rotating 1D array of ultrasound transducers, according to some embodiments;

FIG. 10A through FIG. 10C are the labeled photographs of FIG. 7A through FIG. 7C with the high intensity contiguous reflections from the back of the airway indicated, according to some embodiments;

FIG. 14A through FIG. 14D are graphs that illustrates example dependence of the averaged measured area of high intensity contiguous pixels in a region of interest (ROI) for unobstructed and obstructed airways for four different subjects, according to some embodiments;

FIG. 15A through FIG. 15D are graphs that illustrates example dependence of the individual measured area of high intensity contiguous pixels in a region of interest (ROI) for unobstructed and obstructed airways for four different subjects, according to some embodiments;

DETAILED DESCRIPTION

Figure 1A:
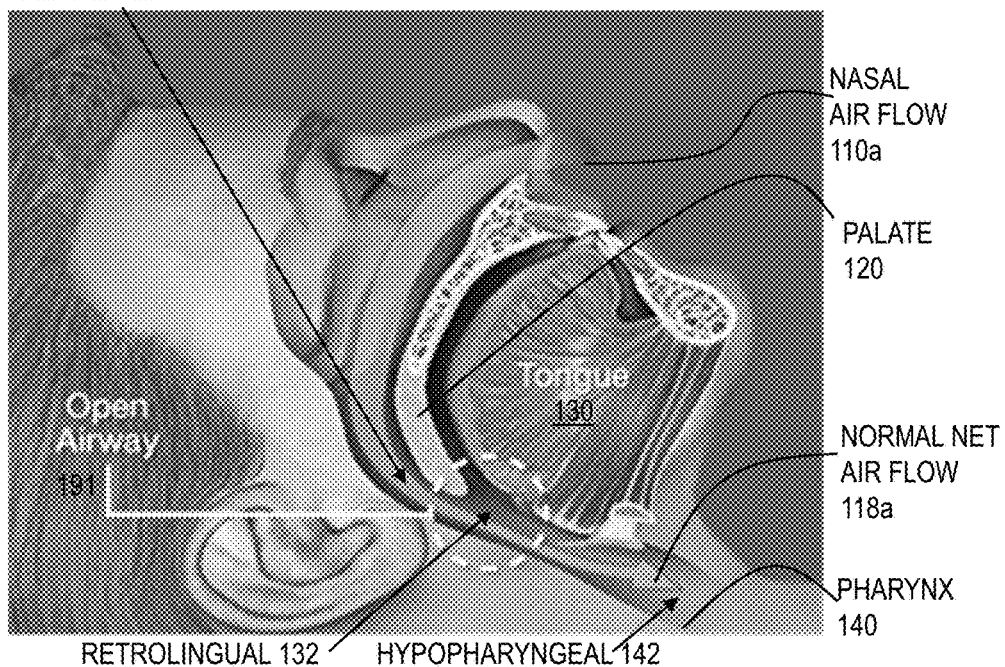
FIG. 1A and FIG. 1B are block diagrams that illustrate example open and obstructed airways, respectively, in a subject.

A method and apparatus are described for the automatic collection of ultrasound imaging data for localization of an obstruction contributing to obstructive sleep apnea. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of ultrasound transducers used in sequence without beamforming to detect reflected energy as a function of time from an airway in a subject. However, the invention is not limited to this context. In other embodiments ultrasound transducers are arrayed to detect transmitted, refracted and scattered energy in addition to or instead of reflected energy from the airway or other tissue structures of the subject, with or without beamforming and with or without computed tomography.

1. Review

Historically, diagnosis of OSA has been achieved through history obtained from the patient and the sleep partner. To increase the sensitivity and specificity of diagnosis, numerous studies have advocated the addition of polysomnographic testing (Riley et al. 1993) that includes a battery of measures including blood oxygenation levels during the apneic episodes, physiological measures such as heart rate, respiratory rate and electroencephalography (EEG). Polysomnography in a certified sleep lab is the gold standard for diagnosis of OSA in current medical care. Other joint task force recommendations (Veasey 2006; Collop 2007) identified a cohort of patients who could be candidates for portable monitoring (PM) through application of probes and sensors that specifically measure physiological parameters during the episodes of apnea. A large volume of literature has thus evolved, concentrating on the following parameters (Collop 2007): 1. Oximetry; 2. Respiratory monitoring including a) Effort, b) Airflow, c) Snoring, d) End-tidal CO2, e) Esophageal pressure; 3. Cardiac monitoring, not limited to: a) Heart rate or heart rate variability, b) Arterial tonometry; 4. Measures of sleep-wake activity such as a) Electroencephalography, b) Actigraphy; 5. Body position; and 6. Miscellaneous others.

While monitoring technology for these measurements has largely been in place especially during polysomnography (PSG) testing, traditionally called a sleep study, these pave the way only for diagnosis and are specifically deficient for accurate localization of obstructive phenomena. The importance of localization (site of obstruction imaging) is in treatment, wherein an area of obstruction could be surgically ameliorated. Thus, diagnosis alone is not sufficient for reducing the progression of the syndrome; and continuous positive airway pressure (CPAP) that works by pneumatically stenting the airway, does not specifically address the site(s) of obstruction. A technique to monitor and identify the site of obstruction could be a significant milestone in formulating long-lasting treatment strategies for an individual diagnosed with OSA.

The simplest method for assessment of airway geometry involves use of the lateral skull and neck radiographs for cephalometric calculations. A summary of these radiographic findings (Deberry-Borowiecky et al. 1988) in these patients include (a) enlargement of the tongue and soft palate. (b) inferior displacement of the hyoid bone (c) normal size and position of the mandible, yet changes in the relative positions of landmarks on the mandible itself (d) backward displacement of the maxilla and elongation of the hard palate and (e) normal nasopharynx, but reduction in the oropharyngeal and hypopharyngeal airway diameters. In combination, these findings illustrate the presence of multi-segmental changes within the aerodigestive tract that may be targeted with surgical procedures (Guilleminault et al. 1984; Riley et al. 1985). However, the major disadvantage with these radiographic assessments concerns simultaneity, i.e. obstructive phenomena may occur at multiple levels but the lack of resolution of x-ray findings prevents categorization of obstruction into major and minor phenomena, hence they lose their relevance for accuracy in localization for targeted treatment. Lateral cephalogram radiography also fails to elucidate the importance of soft tissue in the etiology of apnea. A modified technique for obtaining radiographs, i.e. fluoroscopy, wherein live imaging of the airway could be obtained using continuous x-ray exposure has higher sensitivity and specificity (Pepin et al. 1992). However, somnofluoroscopy is unsuitable for introduction as a screening tool due to exposure to ionizing radiation.

An alternate technique that has been frequently used in literature includes the use of high-resolution CT scans (Bhattacharyya et al. 2000; Rodenstein et al. 1990). Here, the resolution is markedly improved with current technology that permits extremely thin slice acquisitions, and may be combined with a trigger-activated circuitry using pulse oximetry, obtaining scans that may be acquired specifically during the time of obstruction. As promising as it sounds, there are several problems associated with deployment, namely exposure of subjects to high levels of ionizing radiation, loss of natural sleep patterns during acquisition within the scanner bay, and costs. Similar problems exist for use of MRI scanners; even as they increase the resolution of soft tissue imaging (Schwab et al. 2003; Shelton et al. 1993). MRI scanners are noisy, with potential to disrupt sleep; and the time taken for acquisition of images may be prohibitive for large-scale screening; with additional problems associated with motion-artifacts.

One of the earliest studies for localization of OSA obstruction focused on simultaneous monitoring of pressures in the posterior nasopharynx, oropharynx, hypopharynx, and esophagus during overnight polysomnography (Shepard et al. 1990). From the profile of pressures recorded in the upper airway and esophagus, the regions over which the airway collapses during apneic episodes could be determined. While this study yielded the degree of relationship between the pressures and PSG-derived indices, this mandated insertion of monitoring probes invasively within the upper aerodigestive tract and the limitation of the number of subsites indicated that the overall resolution was poor. Others (Chaban et al. 1988) that focused on insertion of catheter-based transducers such as the Millar device also reported benefits in measurement. Conceivable issues with long-term measurements include problems with loss of natural sleep architecture owing to the presence of a device in the upper airway, and safety issues concerning migration and potential for the device itself to cause obstruction. Furthermore, animal models often conclude that there is poor relationship (Hudgel 1986) between pressure gradients measured using deployable transducers and the surgical outcomes following procedures such as uvulopalatopharyngoplasty (UPPP).

In assessments of patients prior to undergoing sleep surgery, a flexible fiberoptic endoscopic examination of the upper airway has been recommended (Croft et al.1991) with some confidence owing to the relative ease of this procedure. However, this technique cannot identify patients who have multisegmental anatomic obstruction (Morrison et al. 1993), and those individuals cannot be accurately tested because the measurements are done in the setting of a clinic in an awake state.

Ultrasound technology has been refined and modified for use in areas such as medical imaging (McNay et al. 1999), non-destructive testing (Silk 1984), industrial processing applications (Ruecroft et al. 2005), cleaning (Muthukumaran et al. 2004), and rangefinding (Kuratli et al. 2000). Devices used for biomedical applications have been repeatedly appraised and found to be safe (Hoskins et al. 2010) and suitable for use in a variety of settings, such as obstetric (Romero 2003) and fetal (Crane et al. 1994) diagnostic techniques, cardiac and vascular applications including devices such as catheters and probes (Gardin et al. 2006; Hamers et al. 2001).

Ultrasonic devices for use in diagnosis of obstructive sleep apnea have not been thoroughly evaluated thus far; an extensive MEDLINE search for terms "ultrasound" and "obstructive sleep apnea" produced just four relevant results. Two of these articles specifically evaluated ultrasound for prediction of difficult laryngoscopy in obese patients (Ezri et al. 2003) and for identification of anatomic landmarks prior to procedures such as tracheostomy and cricothyroidotomy (Kajekar et al. 2010). The third, a dissertation (Girard 2003), evaluated a standard ultrasound system to obtain images of the area of the pharynx involved in OSA and utilized image processing algorithms for detection of obstruction. This work also showed that the extracted active contours of the airway accurately detected its state (open or obstructed) in two dimensional axial images of the pharynx. In addition, the author showed that a motion detection algorithm could quantify tongue base movements. Lastly, yet another manuscript (Siegel et al. 2000) evaluated the relationship between ultrasound-derived images and clinical polysomnographic indices, and found good correlation between multiple variables.

2. Overview

Figure 1B:
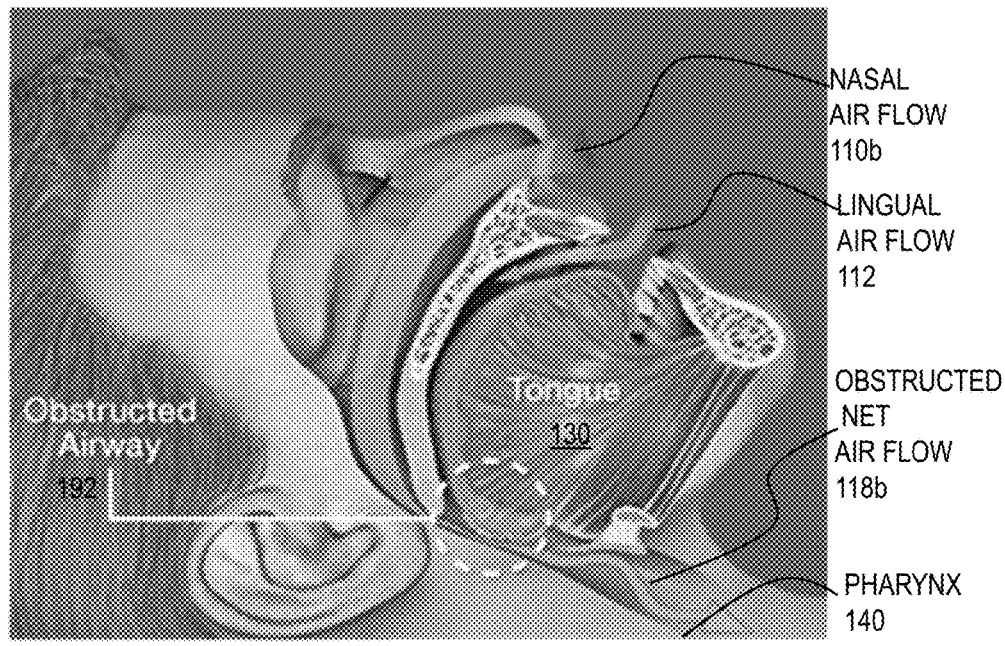

Here is described a method and system that enables one to localize a site of obstruction in patients with OSA using ultrasound technology. To illustrate how the device functions, it is useful to show an example of an airway obstruction in the context of the airway anatomy. FIG. 1A and FIG. 1B are block diagrams that illustrate example open and obstructed airways, respectively, in a subject. The anatomical features of the subject include a soft palate 120, tongue 130 and pharynx 140. An airway is a lumen that includes nasal sinuses inside the nose, a retropalatal portion 122 behind the soft palate 120, a retrolingual portion 132 behind the tongue and a hypopharyngeal portion 142 in front of the pharynx. FIG. 1A depicts normal airflow through the nose (nasal air flow 110a) past the palate 120 and tongue 130 and pharynx resulting in normal net air flow 118a. In particular the airway is open in portion labeled open airway 191. FIG. 1B depicts an obstructed airway 192 in the retrolingual portion of the airway corresponding to open airway 191 in FIG. 1A. This results in obstructed net airflow 118b that leads to mouth breathing indicated by lingual air flow 112, or snoring, or insufficient oxygenation of the subject's blood, or some combination, or worse, leads to essentially zero net flow and risk of death if the subject does not awake in time.

2.1 Structural Overview

Figure 2:
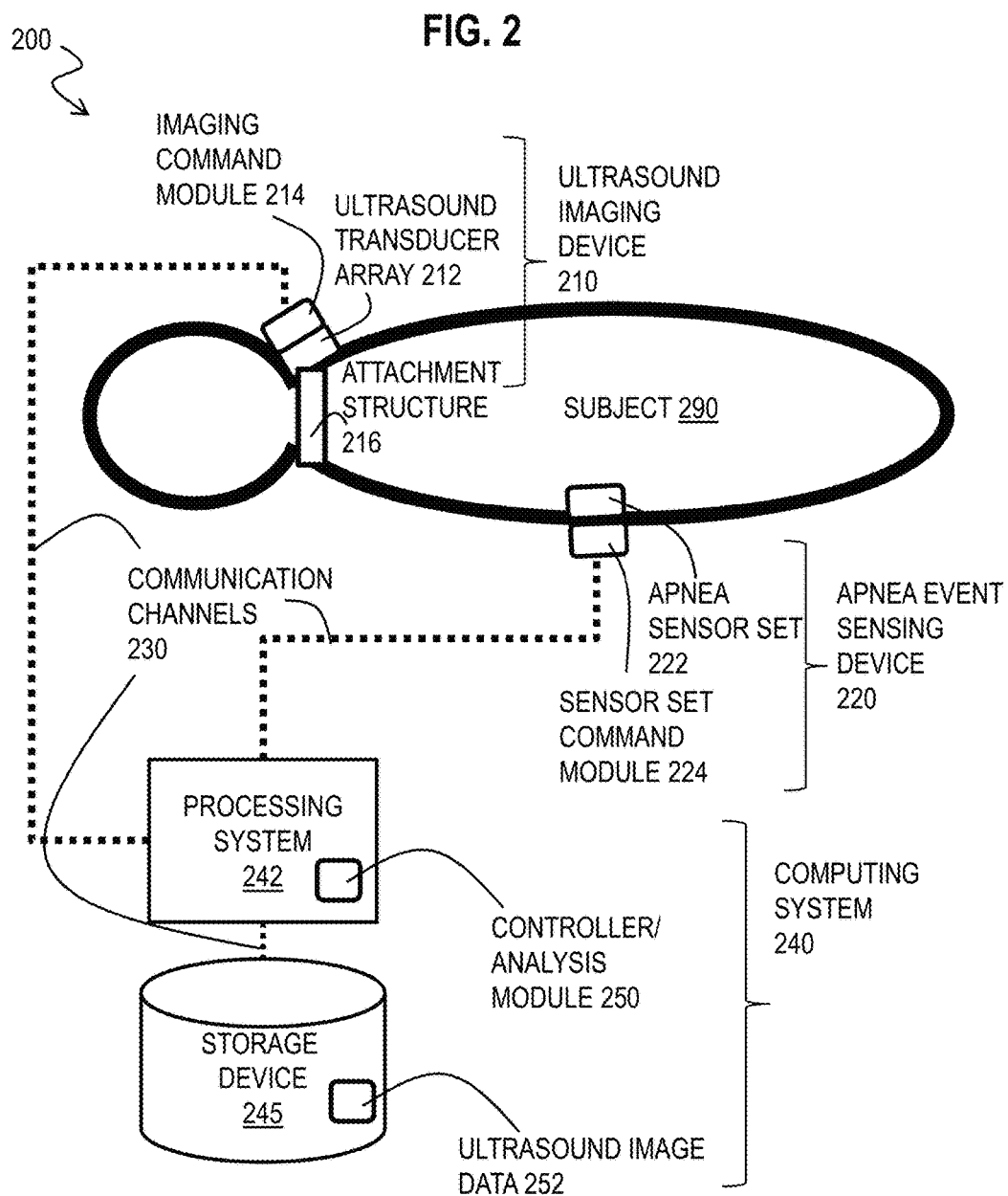
FIG. 2 is a block diagram that illustrates an example system for automatic ultrasound imaging of a subject for determination of location of an obstruction that could contribute to obstructive sleep apnea (OSA), according to an embodiment.

In various embodiments, a system is configured to automatically scan the airway during an obstructive sleep apnea (OSA) event using ultrasound, to provide ultrasound image data that can be used to localize an obstruction, either manually or, in some embodiments, automatically. FIG. 2 is a block diagram that illustrates an example system 200 for automatic ultrasound imaging of a subject for determination of location of an obstruction that could contribute to obstructive sleep apnea (OSA), according to an embodiment. As used herein, a subject can be any organism with lungs, including animals, mammals and humans, alive or dead. Although a subject 290 is depicted for purposes of illustration, subject 290 is not part of system 200.

The system 200 includes an ultrasound imaging device 210, an apnea event sensing device 220, and a computing system 240, in data communication with each other through one or more data communication channels 230.

The illustrated ultrasound imaging device 210 includes an ultrasound transducer array 212, attached to the subject by an attachment structure 216 such as a strap or belt or collar, and a imaging command module 214.

The ultrasound transducer array 212 is a set of two or more ultrasound transducers arranged in one or two dimensions configured to operate together to introduce or detect ultrasound waves. An ultrasound transducer is a component that either produces an ultrasound wave in response to an electrical or optical signal (also called an ultrasound transmitter), or produces an electrical or optical signal in response to an impinging ultrasound wave (also called an ultrasound receiver or detector), or both (also called an ultrasound transceiver). In various embodiments, ultrasound transducers are arrayed to detect transmitted, reflected, refracted or scattered energy from the airway or other tissue structures of the subject, with or without beamforming, and with or without computed tomography. Many ultrasound transducers appropriate for probing human tissues are known in the art and any may be used in various embodiments. Example ultrasound transducers are described below with reference to FIG. 3. The ultrasound transducer array 212 is configured to produce data for multiple ultrasound images representing corresponding multiple cross sections of an airway of the subject 290, as described in more detail below.

The imaging command module 214 is a component that powers and activates the transducer array and transmits data representing the received signals that are used to construct an image. In some embodiments, the command module also constructs the image data based on the received signals. Many ultrasound probes are commercially available with a command module and transducer array as an integrated unit. Examples of such integrated ultrasound probes include: icte and c60e from SONOSITE™ of Bothell, Wash.; 8820e from ANALOGIC™ Corporation, Peabody, Mass.; 10C-D, 10C-SC, 3S-SC, RAB series from GE HEALTHCARE™, Little Chalfont, Buckinghamshire, United Kingdom; EUP-C715, C514, C516, C511, C524 and C532 (convex probes) from HITACHI ALOKA™ Medical America, Wallingford, Conn.; SP2730, CA1123, LA533, LA523 from ESAOTE™ North America, Inc. Indianapolis, Ind.

The computer system 240 is one or more devices, such as a computer system 2000 described in more detail below with reference to FIG. 20, or a chip set, such as chip set 2100 described in more detail below with reference to FIG. 21 and used for example in a portable or mobile device such as a cell phone or tablet. The computer system is configured to control the operation of the ultrasound imaging device 210, and to produce, present or store all or part of the ultrasound image data, or some combination. Many commercially available ultrasound probes are available with terminal equipment that performs some or all of the functions of the computing system 240. Examples of such ultrasound imaging terminals include point of care stations for one or more of the above probes and MyLab Twice, MyLab Seven, MyLab Gold from ESAOTE™ North America, Inc. Indianapolis, Ind.; and, Voluson E10, E8 and E6, Vivid E9, S6, q, S5 LOGIQ e Ultrasound BT 12 from GE HEALTHCARE™, Little Chalfont, Buckinghamshire, United Kingdom.

According to the illustrated embodiment, the computing system 240 includes at least a processing system 242 and storage device 245. The processing system 242 includes hardware and software configured to perform the steps of a novel controller/analysis module 250, as described in more detail below with reference to flow charts in FIG. 4 and FIG. 5A and FIG. 5B. At least some image data that indicates location of an obstruction during an obstructive sleep apnea (OSA) event is stored as ultrasound image data 252 on storage device 245, which is one form of computer-readable memory, as described in more detail below with reference to FIG. 20.

Rather than have the ultrasound imaging device 210 and computing system 240 perform the computationally, algorithmically and power demanding task of constantly imaging the tissues and airways of the subject to determine the timing of an OSA event, the system determines the timing of an OSA event based on a separate apnea event sensing device 220. The device 220 includes an apneas sensor set 222 of one or more sensors that collect measurements that are sensitive to the occurrence of an OSA event, such as interruption of normal chest movement rhythms, a drop in blood oxygen saturation levels, or the interruption of normal acoustic rhythms such as the sounds of breathing or snoring. Sensors typically used for such purposes include microphones to detect the audible sounds made by the subject, blood oxygen saturation sensors such as a pulse oximeter attached to a subject's finger, and one or more accelerometers attached to a subject's chest. The absence of airflow (sensor output) during sleep (EEG) while the chest is moving with resultant decreased saturation (desat) is how a sleep lab would diagnose and OSA event. Example sensors include Airflow sensors, Pulse Oximeter, chest movement sensors, and EEG (to detect sleep), such as SOMNOSTAR™ v4 from VIASYS™ Inc of Conshohocken, PA.; and, e-series and SOMTEPS™ from COMPUMEDICS™, Victoria, Australia. Such sensors are simpler, more rapid or more cost effective than the ultrasound imaging device 210, or offer some combination of these advantages. In some embodiments, it is advantageous to use at least two such sensors, of the same or different types or some combination, to provide reliability and redundancy as a safeguard against failure of a single sensor.

In the illustrated embodiment, the apnea event sensing device 220 includes a sensor set command module 224 to power or control the sensors in the sensor set 222, ensure the sensors are functioning properly, or send an alarm when the sensor data indicates an OSA event, or some combination.

The data communication channels 230 are wired or wireless channels (including BLUETOOTH and WiFi) in direct or networked communication within, between or among two or more of the ultrasound imaging device 210, apnea event sensing device 220 and computing system 240. One or more of the devices 210, 220, 240 is configured to establish communications within or among the devices, for example using standard networking protocols.

The system 200 is configured such that, when an OSA event is detected based on data from the advantageous sensors of the apnea sensor set 222, a signal is sent to the ultrasound transducer array 212 to collect imaging data for forming images of the airway of the subject at multiple cross-sections of the airway, from the retropalatal region down past the hypopharyngeal region. Thus, data is collected that can indicate the location of an obstruction. In some embodiments, a human analyst reviews the images to determine the occurrence of any obstruction. In some embodiments, the system automatically identifies one or more of the images, or regions within the images, or some combination, with features likely to indicate the location of an obstruction.

Although processes, equipment, and data structures are depicted in FIG. 2 as integral blocks in a particular arrangement for purposes of illustration, in other embodiments one or more components or processes or data structures, or portions thereof, are arranged in a different manner, on the same or different equipment, in one or more databases, or are omitted, or one or more different components or processes or data structures are included on the same or different equipment. For example, processing done by the imaging command module 214 or the sensor set command module 224, or both, may be performed in whole or in part by the controller/analysis module 250 in the computer system 240. Likewise, some or all functions performed by the controller/analysis module may be performed by the imaging command module 214 or sensor set command module 224, or some combination.

Thus, the system 200 includes an ultrasound transducer array 212 configured, when disposed adjacent to a neck of a subject 290, to obtain first (imaging) data upon receipt of a signal. The first data supports multiple ultrasound images representing a corresponding multiple cross sections of an airway of the subject 290. The system 200 also includes an apnea event sensor set 222 configured to collect automatically second data sensitive to an apnea event in the subject. The system also includes, in computer system 240 or command modules 214 or 224, at least one processor (e.g., see FIG. 20 or FIG. 21); and at least one computer-readable medium including one or more sequences of instructions. The at least one memory and the one or more sequences of instructions are configured to, with the at least one processor, cause the system 200 to perform at least the following: establish communications with the ultrasound transducer array 212; establish communications with the apnea event sensor set 222; receive the second data; detect an apnea event based on the second data; and in response to detecting the apnea event, cause the signal, which causes the ultrasound transducer array 212 to obtain the first data, to be sent to the ultrasound transducer array 212, and cause image data 252 based on the first data to be stored in a second computer-readable medium, e.g., on storage device 245.

Figure 3:
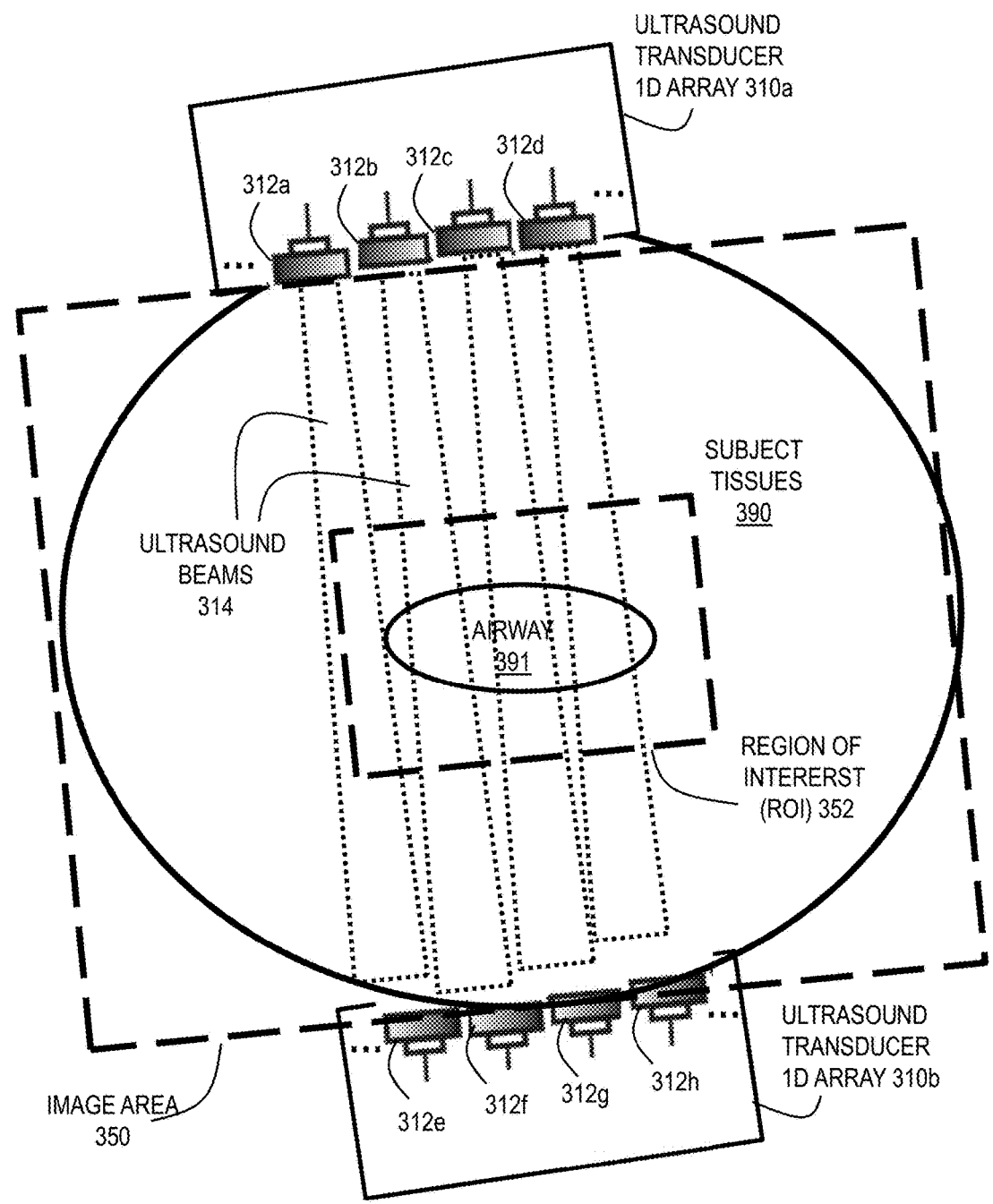
FIG. 3 is a block diagram that illustrates an example one dimensional (1D) array of ultrasound transducers used to acquire a 2 dimensional (2D) ultrasound image, as used according to some embodiments.

FIG. 3 is a block diagram that illustrates an example one dimensional (1D) array 310a of ultrasound transducers 312 used to acquire a 2 dimensional (2D) ultrasound image having image area 350, as used according to some embodiments. The array 310a made up of multiple individual ultrasound transducers 312a, 312b, 312c, 312d, among other represented by ellipsis, and collectively referenced herein as transducers 312. The array is useful for forming ultrasound images based on ultrasound reflective modes and backscattering modes. In some embodiments using ultrasound transmission and refractive modes, a second 1D array 310b is also included, which includes ultrasound transducers 312e, 312f, 312g and 312h, among others indicated by ellipses, and also collectively referenced herein as transducers 312.

In some embodiments, all the transducers are of the same construction. In other embodiments, various individual transducers differ from others. For example, in some embodiments, transducers 312 of array 310a are ultrasound transmitters only and transducers 312 of array 310b are ultrasound receivers only. In some embodiments, one or more transducers are transceivers (both transmitters/emitters and receivers/detectors). In some embodiments, at least some transducers 312 produce longitudinal ultrasound waves in which medium particle displacement is parallel to the direction of wave propagation. In some embodiments, at least some transducers 312 produce transverse ultrasound waves (also called shear waves) in which medium particle displacement is perpendicular to the direction of wave propagation. In some embodiments, some transducers produce both.

Each transducer has an inherent beam pattern, i.e., the produced or detected ultrasound wave varies in intensity in different directions due to constructive and destructive interference from ultrasound emanating from or impinging on different portions of the transducer. In some embodiments, in a well-known process called beamforming, multiple transducers can be operated together to control the timing and location of constructive and destructive interference to form a beam of different width and direction from that of a single transducer. Thus, the beam may be composed and steered under direct computer control. The primary beams 314, whether inherent or beam-formed, of the corresponding transducers 312 of array 310a are depicted in FIG. 3.

When ultrasound transmitters are disposed to introduce one or more ultrasound beams into a medium, the ultrasound may be subsequently reflected, scattered, transmitted and refracted, depending upon the acoustic properties of that medium, such as density and speed of sound. The reflected, scattered, transmitted and refracted ultrasound is then detected by the ultrasound detectors. An image is composed based on the detected sound.

For example, using reflective mode ultrasound imaging, the array 310a of transceiver transducers (that both emit ultrasound and detect it) is operated so that an ultrasound pulse is projected along each beam 314 into a medium. Due to boundaries between materials with different acoustic properties in the medium, or individual scatterers therein, as the pulse encounters such boundaries or scatterers, a portion of the energy is returned within the beam in the opposite direction, eventually reaching the transducer (or phased transducers) where the energy is detected. When the returned energy is plotted as a greyscale against the time of the return, a line of greyscale pixels (also called a scan line) for an image is produced. Depending on the temporal resolution of the detector, this temporal trace can include several hundred to several thousand pixel values. By repeating the process for the next beam, the next line of grayscale pixels can be produced; and, an image can be produced which is composed of the set of all such scan lines. The temporal trace of the returns can be associated with different distances into the medium along the beam based on a known or estimated average speed of ultrasound over that distance.

In embodiments described below, each scan line includes 2400 pixels and corresponds to about 600 pixels per inch (for a scan line of about 4 inches, or about 10 cm).

In order to reduce the effect of scattering from one beam into another beam, the array is often operated so that ultrasound pulses are projected along each beam produced by the array in sequence, one beam after the other, with time between pulses sufficient to allow all returns of interest from the medium along one beam. For imaging of human tissue (sound speed about 1500 meters per second) to depths of about 10 centimeters, the time between pulses is on the order of 1 microsecond ($\mu s$, 1 $\mu s=10^{-6}$ seconds). Thus data to support an image composed of 2400 scan lines can be acquired in less than 0.01 seconds. Multiple images providing different cross sections of the tissue are then collected by moving (e.g., sliding or pointing) the ultrasound transducer 1D array, or including one or more other ultrasound transducer 1D arrays that are offset in a perpendicular dimension to produce a two-dimensional (2-D) array. Thus, in some embodiments, the ultrasound transducer array comprises a two dimensional array. Even if each beam is pulsed sequentially, about 200 images can be collected in about 2 seconds.

Many conventional ultrasound reflective mode probes are composed of a single fixed transducer composed of a monolithic ultrasound-emitting crystal that must be moved in a direction of interest (e.g. along a line) in order to sweep a beam over an area that is being physically examined. A typical example is a probe used in fetal sonography, wherein a probe is physically moved over the maternal abdomen. In contrast, the phased array (PA) reflective mode probe consists of small individual ultrasonic transducers, each of which can be pulsed independently, as depicted above as ultrasound transducer array 310a. A PA probe offers a further advantage in that the design may be constructed of solid-state components only, eliminating noise associated with moving parts for acquisition, decreasing power requirements and an increase in data being generated, and improving the sensitivity of each scan.

In embodiments using transmissive mode, the pulse output along a beam is detected by a transducer array on an opposite side of a medium, e.g., by array 310b, at a time delay based on the average speed of sound through the medium. The detected signal can be affected by refraction if there are sound speed variations in the medium causing different or multiple transducers to detect the pulse. With transmission and refraction detections, it is possible to create an image of sound speed variations, and thus material changes, in the medium using any known techniques of computed tomography.

For various embodiments, the ultrasound transducer array 310a, or 310b or both, is configured to detect an airway 391 among subject tissues 390, which together comprise the medium to be imaged. An important consideration during acquisition of these images pertains to the quality of images due to presence of multiple layers of tissues. In addition, the tissue interfaces at each level demonstrate different acoustic properties, some of which are extremely dense sonographically, e.g. bone. This has been circumvented by the use of a transducer array spread over a large surface area and focusing/steering of the wavefront using beam forming. There exists an application of this technology for focused intracranial ultrasound, and the potential for development of completely non-invasive ultrasonic scalpels in neurosurgery (Clement 2000).

At least two types of transducer are suitable for various embodiments. Conventionally, contact transducers use a thin layer of gel or other types of impedance matching material to drive ultrasound waves into a medium of variable acoustic properties (anisotropy). However, over the last decade, there has been an increased interest in non-contact ultrasound (NCU) that does not need an intervening layer of a medium with low acoustic impedance. These offer the advantage of ease of use and more comfort for the subject. NCU arrays utilize electromagnetic acoustic transducers (EMAT) that rely on generation of a sound signal in a target material adjacent to the probe but not in contact with the probe. Each EMAT element is composed of an electric coil driven with an alternating current (AC) electric signal at ultrasonic frequency, typically in the range from 20 kHz to 10 MHz. The electric signal generated could be modulated in any fashion, e.g. a continuous wave, a spike pulse, or a tone-burst signal. The electric coil with AC current also generates an AC magnetic field. When the target material is close to the EMAT, ultrasonic waves are generated in the target material through the interaction of the two fields.

In various embodiments, not all the tissue in the subject is imaged, only tissues in the vicinity of the airway. Thus a reflective mode ultrasound transducer array that extends along one full side of image area 350 encounters more different tissues and materials, including materials outside the subject, than are needed for assessing whether an airway 391 is open or obstructed. Thus for each image obtained from each ultrasound transducer array 310a, a subset of pixels in a region of interest (ROI) 352 is defined such that the ROI 352 encompasses the airway. This can be done manually or automatically based on landmarks in the image, such as the spine and the teeth and trachea and the high reflectance from the back of the airway, which are readily recognizable. The landmarks and the ROI are expected to vary as one follows the airway through the body. As described in more detail below, different images are grouped into different anatomical domains such as retropalatal, retrolingual, hypopharyngeal and mid-tracheal. However, for a transducer array fixed with respect to the subject, the anatomical domain and the ROI can be defined once and then used for all subsequent images from that transducer array.

2.1 Method Overview

FIG. 4 is a flow diagram that illustrates an example method 400 for automatic ultrasound imaging of a subject for determination of location of an obstruction that could contribute to obstructive sleep apnea (OSA), according to an embodiment. Although steps are depicted in FIG. 4, and in subsequent flowcharts FIG. 5A and FIG. 5B, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 401, an ultrasound transducer array 212 is provided, such as array 310a, and is configured to produce first data (e.g., reflection or transmission temporal profiles along each of multiple beams formed by the array) for a high resolution image (e.g., with a range from about 0.1 to about 2.0 millimeters (mm) of organic tissue at depths into the tissue from about 2 to about 6 cm in each of multiple cross sections (also called slices), e.g., by pointing or sliding or with a 2-D array. Transducer frequencies of 1 to 10 MHz provide an axial resolution from about 0.15 mm to about 1.50 mm. In images, this ranges from about 50 dots per inch (dpi) and above (corresponding to 20 pixels/cm and above). Above about 600 dpi, disadvantages include increase sensor noise and increased demands for storage of data. In experimental embodiments, described in more detail below, the airway is at least 3 cm deep. It is advantageous to achieve a depth of penetration of about 5 cm to include the anterior spine. A transducer frequency of about 7 MHz and below is advantageous for providing optimal resolution at the deepest tissues in the region of interest (ROI).

In step 403, a sensor set 222 is provided, and is configured to measure second data (e.g., blood oxygen saturation, chest movement, breathing sound, among others, or some combination) sensitive to obstructive sleep apnea (OSA) events in a subject.

In step 405, communication channels 230 are provided between a computer system 240 and both the ultrasound transceiver array 212 and the sensor set 222, either directly or indirectly through command modules 214, 224, respectively.

In step 407, the computer system 240, including any terminal provided with the transducer array 212, is configured, either by software or special purpose circuitry or some combination, to perform several functions. Those functions include operating the array to obtain one or more images during normal breathing; detect an OSA event based on second data communicated from the sensor set; in response to detecting the OSA event, cause the ultrasound transceiver array to collect data during the event; and present ultrasound images that indicate location of obstruction in one or more of the multiple cross sections, including storing one or more such images.

In step 411, the ultrasound transceiver array 212 is placed adjacent to a subject 290 in a position to produce images corresponding to cross sections (slices) of a subject airway from retropalatal to mid tracheal anatomical domains. For example, the ultrasound imaging device 210 (also called an ultrasound probe) is removably attached to the subject with an attachment structure 216 that keeps the array 212 near to, or in contact with, the skin of the subject 290. In some embodiments, step 411 includes operating the transducer array to collect first data for one or more images that represent corresponding cross-sections in one or more anatomical domains during normal breathing or normal (non OSA event) sleep.

In step 413, the sensor set 222 in placed in position to detect an OSA event in the subject 290. For example, a pulse oximeter is placed on a finger of the subject, and a microphone is placed on the head of the subject. In some embodiments, one or more sensors is configured to automatically alarm, which alarm can be used as a triggering event. For example, some telemetric pulse oximetry probes automatically send an alarm when oxygen saturation falls below a set threshold, such as 90% $SpO_2$.

In step 415, the computer system 240 is operated to present one or more images that indicate a location of an obstruction in the subject, including storing one or more images as image data 252, based on the first data. In some embodiments, the computer system 240 also automatically indicates one or more images, or one or more sub-images (portions of the images), where an obstruction is likely to be indicated.

In step 417, the subject is treated based on the location of an obstruction in an image of the one or more images presented or stored in step 417. For example, if no obstruction is indicated, the patient is treated for a syndrome other than OSA. If an obstruction is identified and located, then a surgical procedure is performed on the subject, e.g., to biopsy or remove a foreign object, if any, or to introduce an object or remove tissue to prevent obstruction at that location by indigenous tissues. In some embodiments, the location of the obstruction is not automatically determined by the computer system; and, a human analyst uses the images presented by the computer system in step 415, and the human analyst determines the location of an obstruction, if any.

In step 419, it is determined whether there is another subject to examine. If not, then the method ends. Otherwise, control passes back to step 411 to place the transducer array on the next subject, and perform the following steps.

FIG. 5A and FIG. 5B are flow diagrams that illustrates example methods for automatic determination of location of an obstruction in ultrasound images, according to an embodiment. FIG. 5A illustrates an example method 500 for initial operation of the transducer array, including steps 501 through 523. Method 500 is an example embodiment of a portion of step 411 for initial placement of the transducer array on the subject, of the method 400 of FIG. 4.

In step 501, each portion of the ultrasound transducer array is associated with a location in the subject and one of two or more anatomical domains, such as the retropalatal domain, retrolingual domain, hypopharyngeal domain and mid-trachea domain, the latter where the trachea is evident in an image below the hypopharyngeal domain. For example, transducers 312a through 312d are associated with the airway 391 on one cross section of the subject, e.g., a slice perpendicular to the neck at the location of the array 310a, and the corresponding anatomical domain, e.g., the hypopharyngeal domain. After spatial tagging (co-registration), the acoustic impedances are monitored during obstructed cycles, as described below.

In some embodiments, step 501 includes defining the region of interest (ROI) for each cross section. In embodiments that use the spine as a landmark for the ROI, it is noted that a signal is completely attenuated as it reaches the interface in the posterior aspect of the spine. As the spine and tissues behind it (including muscle and ligaments) are relatively thick, the point of maximum attenuation defines the posterior limit of the ROI. The anterior limit of the ROI is advantageously defined by reflectance properties of the air-tissue interface in an unobstructed airway. Similarly, transducers placed on the lateral aspect of the neck also depend on ultrasound reflection across tissue-air interface where the wave fronts are incident laterally. In a normal unobstructed airway, this represents the air-tissue interface defined by maximal changes in acoustic impedances. As the cervical spine has a bony component all the way to the base of the skull, this determines how far vertically images are conveniently obtained. This also applies to the transducer capturing images from placement just at the level of the sterno-clavicular joint (transition from neck to chest) as the angled wavefront will be scattered by the chest wall.

In step 503, the next ultrasound image is obtained. Any method may be used to obtain the next ultrasound image. For example, in various embodiments, the first data is obtained from the transducer array 212 or the imaging command module 214 or both, and the data is transformed into image data by the controller/analysis module 250, or the image itself is obtained from the imaging command module 214 that determines the image, or the image is retrieved from data storage device 245 where it was stored by the imaging command module 214 or the controller/analysis module 250.

Step 503 includes associating the next image with the corresponding cross-section location and the associated anatomical domain. In the illustrated embodiment, step 503 includes extracting the pixels of the sub-image in the region of interest (ROI) that is known to encompass the airway on the corresponding cross section as a result of step 501.

In the illustrated embodiment, during step 503, the image is also associated with a portion of the respiratory cycle, e.g., such as inhale portion or exhale portion, or sub-portions therein. Any method may be used to associate the image with a portion of the respiratory cycle. For example, in various embodiments, the image is associated with time and a separate data file is created recording data responsive to breathing phenomena versus time, such as a temporal recording of breathing sounds or airflow at the nose or mouth or both of the subject. In other embodiments, the image is collected in response to an automatic or manual trigger based on the respiratory cycle, e.g., at start of inhale and end of inhale, as determined, for example, using airflow sensors and chest movement sensors.

In step 505, a histogram of pixel count for each interval of pixel intensity (e.g., grayscale value) levels (called hereinafter a pixel intensity histogram, or simply intensity histogram) is determined in the ROI sub-image. See FIG. 12A, described below for an example intensity histogram 1216 in a ROI sub-mage during normal breathing. In the presence of an open airway, there is a bright return from the back of the airway (i.e., the side of the airway farthest from the transmitting transducer) due to the relatively large difference between the acoustic properties of the air in the airway and of the tissue at the back of the airway. Thus the histogram shows a wide range of intensity values. In some embodiments, the histogram is normalized so that a maximum value (e.g., 255 corresponding to an eight bit binary number) corresponds to the maximum intensity observed in the ROI for the corresponding cross-section during all normal breathing images of the same cross section. Such bright returns ae lacking in cross-sections in which the airway is obstructed, as described in more detail below with reference to FIG. 8A and FIG. 9A.

In step 507, a threshold pixel intensity value is determined that characterizes the intensity at the airway tissue interface at the back of the airway. In an illustrated embodiment, this threshold is selected as a value two standard deviations above the mean intensity value. See FIG. 12A, described below for an example mean value 1217 of the intensity histogram 1216.

In step 509, candidate sets of contiguous pixels that exceed the threshold are determined. Contiguous pixels that exceed the threshold are pixels that are adjacent and above the threshold. A candidate set of contiguous pixels that exceed the threshold is constructed, for example, by added to the set any pixel that exceeds the threshold and is adjacent to a pixel already in the set, starting from an initial pair of contiguous pixels. There are often multiple candidate sets of contiguous pixels in a ROI. For each candidate set, a property of the set is determined, such as the total number of pixels, total area (e.g., total number of pixels times the area associated with each pixel), maximum extent (difference between largest pixel row or column and smallest pixel row or column, or some combination, such as a Euclidean distance between the smallest row and column to the largest row and column), maximum intensity, average intensity per pixel in the set, integrated intensity, major and minor axis lengths of smallest enclosing oval, a center of intensity (e.g., an intensity weighted center of the set), a first or higher moment of intensity distribution, among others, alone or in some combination.

In step 511, the candidate set, and its value of the property, is not used in further analysis, if a size of the candidate set is less than a threshold size (e.g., a length of the candidate contiguous set is less than 1 cm). Each remaining set is called a selected set of contiguous pixels above the threshold, or simply a selected set.

In step 513, a statistic (such as the sum or mean) of all the selected sets in the ROI is determined. In an illustrated example, the total area of the selected sets is determined. In step 515, the statistic is accumulated over the same transducer portion determined in step 501, for multiple images selected at different times, such as during different portions of the respiratory cycle. For example, the current value of the statistic is stored with data indicating the subject, the current date, the transducer portion, the ROI, and the portion of the respiratory cycle.

In step 517, it is determined whether there is another image to be collected during normal breathing, e.g., at a different transducer portion or different cross-section or different portion of the respiratory cycle. If so, control passes back to step 503 and following steps. If not, then control passes to step 521.

In step 521, principal component analysis is performed on the accumulated statistics to characterize normal conditions. Any known principal component analysis can be used. For example, a mean and standard deviation is determined for each cross-section ROI or anatomical domain. In an illustrated embodiment, a scatter plot of the statistic (e.g., total area of selected sets of contiguous pixels that exceed the threshold) against time for all cross-sections in each anatomical domain is used to define principal components of the variability in that anatomical domain. In some embodiments that do not perform automated identification of obstruction location, step 521 is omitted.

In step 523, cluster analysis of the principal components is performed to characterize any similarities or differences in normal respiration among the different anatomical domains. Any known cluster analysis can be used. In some embodiments, the signal-to-noise ratio (SNR) is examined first by attachment of an anecdotal probe and the analysis unit completes a first pass scan and ensures good SNR. Alternatively, this scan determines the ratio of the variance of a proposed index of measurement (e.g. airway diameter, established by acoustic properties alone) at a given set of coordinates and the mean of the same measurement over a number of trials of respiration taken over discrete time windows. A Fano Factor, FF, is determined in some embodiments, as given by Equation 1.

$$FF = \sigma^2/\mu \quad (1)$$

Where $\sigma$ is sample variance and $\mu$ is sample mean. High Fano Factor implies high variability and low reliability; low Fano Factor indicates the opposite. If a probe array shows high Fano Factor, it is adjusted for better performance or swapped for another probe of alternate geometric design. These steps are also applicable when it is desired to image a fixed obstruction in more detail. FF in such an instance would be less than zero. In some embodiments, the property is airway diameters measured as a function of distance from a fixed point such as the mandible, in three different axes. In these embodiments, a trainable classifier is used that predicts the identity of a particular location in the three axes after subjecting it to a 'training period' wherein the classifier learns the variability of different levels of airway diameter with normal breathing, as identified by the pulse oximeter. In some embodiments that do not perform automated identification of obstruction location, step 523 is omitted.

FIG. 5B illustrates an example method 550 including steps 551 through 573 for operation of the transducer array, in response to detecting an OSA event. Thus, method 550 is an example embodiment of step 415 of the method 400 of FIG. 4.

In step 551, the next ultrasound image is obtained during the OSA event. Any method may be used to obtain the next ultrasound image, as described above for step 503. Step 551 includes associating the next image with the corresponding cross-section location and the associated anatomical domain. In the illustrated embodiment, step 551 includes extracting the pixels of the sub-image in the region of interest (ROI) that is known to encompass the airway on the corresponding cross section as a result of step 501.

In step 553, a histogram of pixel count for each interval of pixel intensity is determined in the ROI sub-image. In some embodiments, the histogram is normalized so that a maximum value (e.g., 255 corresponding to an eight bit binary number) corresponds to the maximum intensity observed in the ROI for the corresponding cross-section during all normal breathing images of the same cross section, as defined above for step 505. Because bright returns are lacking in cross-sections in which the airway is obstructed, the histogram is shifted to lower values for at least one cross-section during an OSA event. See FIG. 12B, described below, for an example histogram of an ROI encompassing an obstructed airway when a histogram is normalized to the maximum intensity during normal breathing, as described here.

In step 555, candidate sets of contiguous pixels that exceed the threshold defined in step 507 of the method 500 of FIG. 5A are determined. There are expected to be fewer candidate sets of contiguous pixels in a ROI encompassing an obstructed airway. For each candidate set, the value of the property of the set is determined, as described above for step 509 of method 500 in FIG. 5A.

In step 557, as in step 511 of the method 500 in FIG. 5A, the candidate set, and its value of the property, is not used in further analysis, if a size of the candidate set is less than a threshold size (e.g., a length of the candidate contiguous set is less than 1 cm).

In step 559, the statistic (such as the sum or mean) of all the selected (non-discarded) sets in the ROI is determined, as described above for step 513 of method 500 in FIG. 5A. For example the total area of the selected sets is determined.

In step 561, the value of the statistic on the current image is compared to the values of the same statistic accumulated over the same transducer portion during normal breathing as described above for step 515 of method 500 in FIG. 5A.

In step 563, it is determined whether the difference between the current value and the mean of the distribution of values for normal breathing is outside the normal range, e.g., the probability of being from the same distribution of values is less than about 5%. If so, then control passes to step 565. If not, then control passes to step 567.

In step 565, the ROI of the current image is marked as indicating a candidate obstruction. For example, the ROI is stored as ultrasound image data 252 along with data indicating a candidate obstruction, data indicating the cross section corresponding to the image from which the ROI was selected, data indicating the time, the date and the subject. In some embodiments, a more comprehensive analysis can be made available offline or be printed to be provided in the same format as a polysomnography record. Control then passes to step 567.

In step 567, it is determined whether there is another image to be collected during the same OSA event, e.g., at a different transducer portion or different cross-section. If so, control passes back to step 551 and following steps. If not, then control passes to step 571.

In step 571, it is determined whether there are a sufficient number of OSA events for each ROI to statistically characterize the variability and select among the candidate ROIs automatically with some statistical confidence. For example, it is determined whether a dozen or more events have occurred over the course of several days or a week or longer. If so, then control passes to step 573 to perform an automated analysis. If not, then control passes to step 551, or the process ends. In some embodiments that do not perform automated analysis or selection among candidate ROI, step 571 is omitted.

In step 573, cluster analysis of principal components is performed over multiple OSA events to characterize most probable location and ROI for intervention to mitigate obstruction to reduce or eliminate future OSA events. For example, the candidate ROI, or candidate ROI cluster, with principal component coefficients outside of all clusters associated with normal breathing and the farthest from any such cluster would be considered as the ROI most likely to encompass the worst obstruction. In some embodiments, using airway diameters in three axes as the property, the classifier examines the variability in airway diameter to determine if it lies outside the variability during normal breathing.

In some embodiments, the automated detection scores a 'hit' when a region of the airway/neck demonstrates variability that is an outlier to the normal distribution of variance of neck airway cross-sectional sizes during unobstructed breathing. Once this location is determined, the transducer array is operated to complete a second order scan wherein the array obtains scans of the area of obstruction at a much higher resolution; and the analysis is repeated.

In some embodiments, a method to determine sensitivity, specificity, receiver operating characteristics, or false discovery rate, or some combination, is incorporated to assess accuracy of detection. For example, in some of these embodiments, based on regularized methods of regression analysis, the threshold for detection is altered for enhanced sensitivity.

After step 573, the process ends. In some embodiments that do not perform automated analysis or selection among candidate ROI, step 573 is omitted; and, the process simply ends.

Thus is presented a novel device and system and method that enables the localization of a site of obstruction in patients with OSA using ultrasound technology. Some advantages are listed here. (a) The system and method are convenient. The test may be conducted entirely at home with preservation of natural sleep structure. (b) The system and method are non-invasive. The appliance is limited to skin surface application, with no probes inserted into the airway. (c) The system and method are inexpensive. The device itself utilizes ultrasound imaging technology with use of disposable and/or reusable supplies. (d) The system and method are safe. They do not use harmful radiation modes and they have little to no moving parts. (e) The system and method are retestable and reliable. The device may be deployed continuously over several nights for acquisition of data, increasing the sensitivity and specificity of diagnosis. (f) The system and method are amenable to remote acquisition and control. By linking via internet, the proposed system is suitable for remote back up of data with complete control by the test administrator remotely.

3. Example Embodiments

Various example embodiments are describe in this section, including simulated embodiments with 2D transducer array, and experimental embodiments conducted with a cadaver as a subject using a rotating 1D transducer array.

3.1 Rotating 1D Transducer Array Without Beamforming

Figure 6:
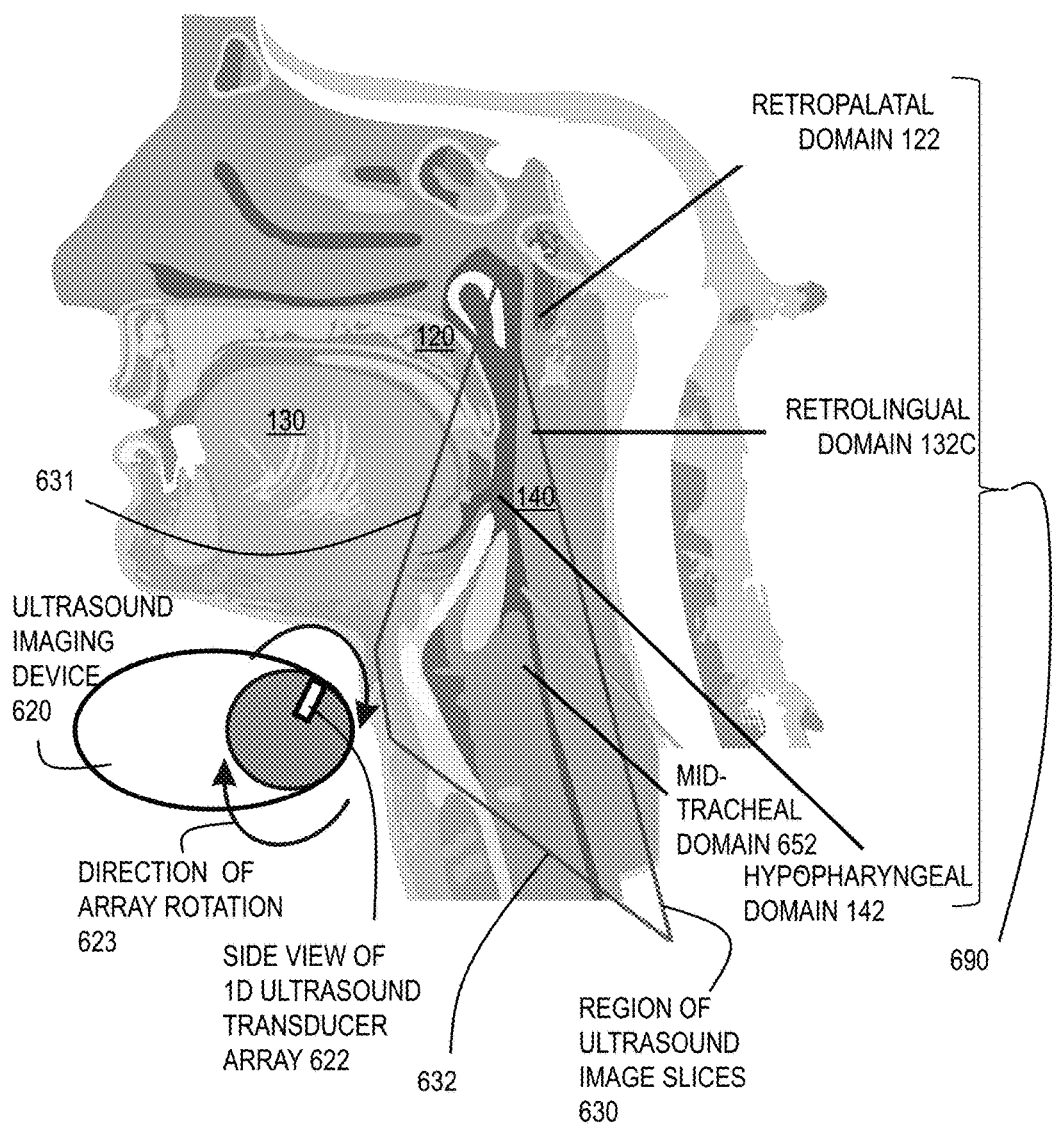
FIG. 6 is a block diagram that illustrates an example rotating 1D array of ultrasound transducers used to acquire multiple 2D ultrasound images, as used according to some embodiments.

FIG. 6 is a block diagram that illustrates an example rotating 1D array 622 of ultrasound transducers used to acquire multiple 2D ultrasound images, as used according to some embodiments. The array 622 is depicted in side view looking along the axis of rotation so that the angular rotation is in direction 623. The rotating 1D array 622 is housed in an ultrasound imaging device 620, which can be held in place to simulate a device strapped to the throat of the subject 690. Although depicted for purposes of illustration, the subject 690 is not part of the device 620.

In one orientation, the 1D array 622 produces a 2D image along a cross section perpendicular to the view of FIG. 6 along a top side 631 of trapezoidal region 630. In a different orientation, the 1D array 622 produces a 2D image along a cross section perpendicular to the view of FIG. 6 along a bottom side 632 of trapezoidal region 630. In between these two images, multiple 2D images are produced along intervening cross sections. Note that the cross sections are not parallel in this embodiment, but yet sample the airway from the retropalatal domain 122, through the retrolingual domain 132 and the hypopharyngeal domain 142 to the mid-tracheal domain 652.

To study the automated identification of an ROI encompassing an obstruction, the ultrasound imaging device 620 was used in an experimental embodiment in which the subject was a cadaver. The cadaver was surgically altered to allow tissue collapse to be induced. Soft tissue collapse was induced by application of sustained negative pressure (−5 cm of water) via a reversed tracheostomy tube. This negative pressure just exceeds the mean critical pharyngeal closing pressures in humans.

FIG. 7A through FIG. 7C are labeled photographs that illustrate example regions of interest of images that represent three cross sections of an airway of a subject based on data collected from the rotating 1D array of ultrasound transducers, according to some embodiments. The imaging device is in a relative direction toward the bottom of each ROI; and, the cadaver airway was left open for all three ROI. FIG. 7A illustrates an example retropalatal ROI 720 that includes airway 729 as a dark area between tissues with reflective returns indicated by the light pixels. FIG. 7B illustrates an example retrolingual ROI 730 that includes airway 739 as a dark area between tissues with reflective returns indicated by the light pixels. FIG. 7C illustrates an example mid trachea ROI 740 that includes airway 749 as a dark area between tissues with reflective returns indicated by the light pixel, including a distinctive bright return from the curved front (anterior)portion of the airway.

FIG. 8A through FIG. 7F are labeled photographs that illustrate example regions of interest (ROI) of images that represent six cross sections for an unobstructed airway of a subject based on data collected from the rotating 1D array of ultrasound transducers, according to some embodiments. These ROI are from images representing cross sections of the cadaver with an open airway. In the presence of an air column in the upper airway, images acquired by the transducer contain a consistent bright stripe highlighted by dashed ovals 821, 822, 823, 824, 825 and 826 in the 6 panels of ultrasound image ROIs in FIG. 8A through FIG. 8F, respectively. These bright stripes represent increased acoustic impedance at the boundary between the airway and the tissues in back of the airway.

Subsequent to application of negative pressure, the bright stripe disappears in spatially aligned images as shown in FIG. 9A through FIG. 9F. FIG. 9A through FIG. 9F are labeled photographs that illustrate example regions of interest of images that represent the same six cross sections for an obstructed airway of the same subject based on data collected from the rotating 1D array of ultrasound transducers, according to some embodiments.

FIG. 10A through FIG. 10C are the labeled photographs of FIG. 7A through FIG. 7C with the high intensity contiguous reflections from the back of the airway indicated within ovals 1010a, 1010b and 1010c, respectively, according to some embodiments. These bright areas are captured as example selected sets of contiguous pixels during normal breathing according to the method of FIG. 5A.

Figure 11A:
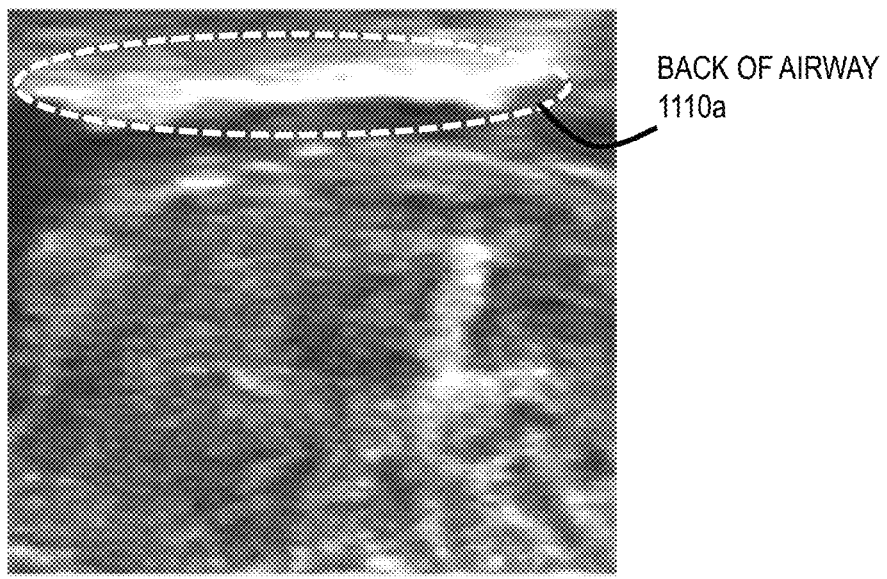
FIG. 11A and FIG. 11B are labeled photographs that illustrate example images that represent the sections for an unobstructed airway and an obstructed airway, respectively, of the same subject, according to some embodiments.
Figure 11B:
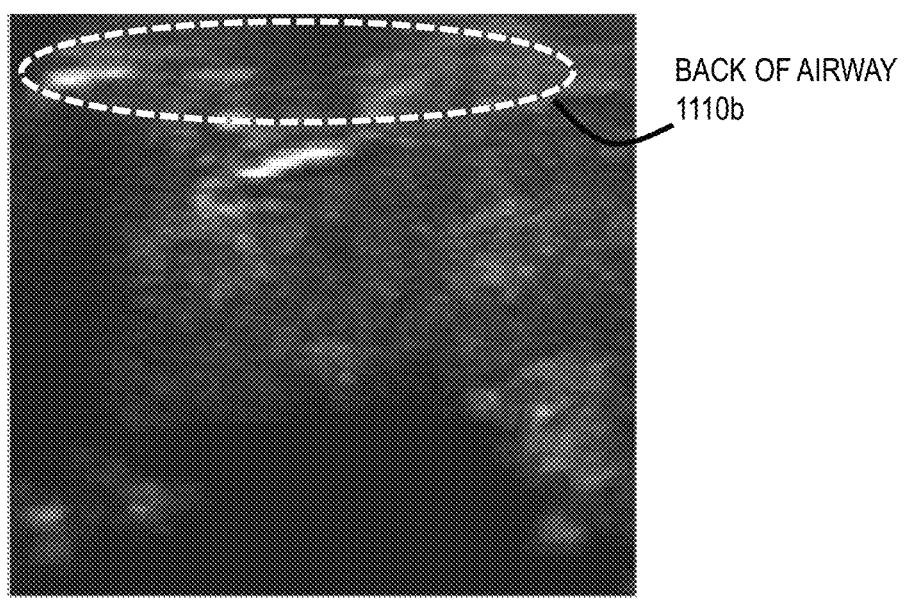

Such edges can discern the air-tissue interface from the rest of the image. FIG. 11A and FIG. 11B are labeled photographs that illustrate example ROIs of images that represent the same cross-sections for an unobstructed airway and an obstructed airway, respectively, of the same subject, according to some embodiments. The edge is apparent in FIG. 11A in one slice in an unobstructed cadaver as enclosed by oval 1110a. In a similarly oriented slice FIG. 11B in the same cadaver under obstructed conditions, application of the same algorithm shows relative diminution of the air-tissue interface enclosed by oval 1110b.

Figure 12A:
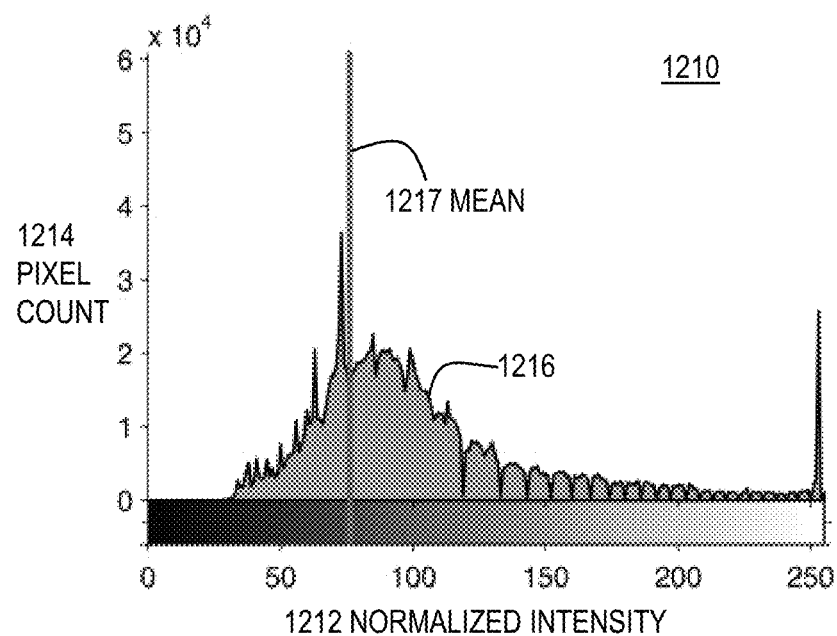
FIG. 12A and FIG. 12B are graphs that illustrate example histograms of pixel intensities for the images of FIG. 11A and FIG. 11B, respectively, according to some embodiments.
Figure 12B:
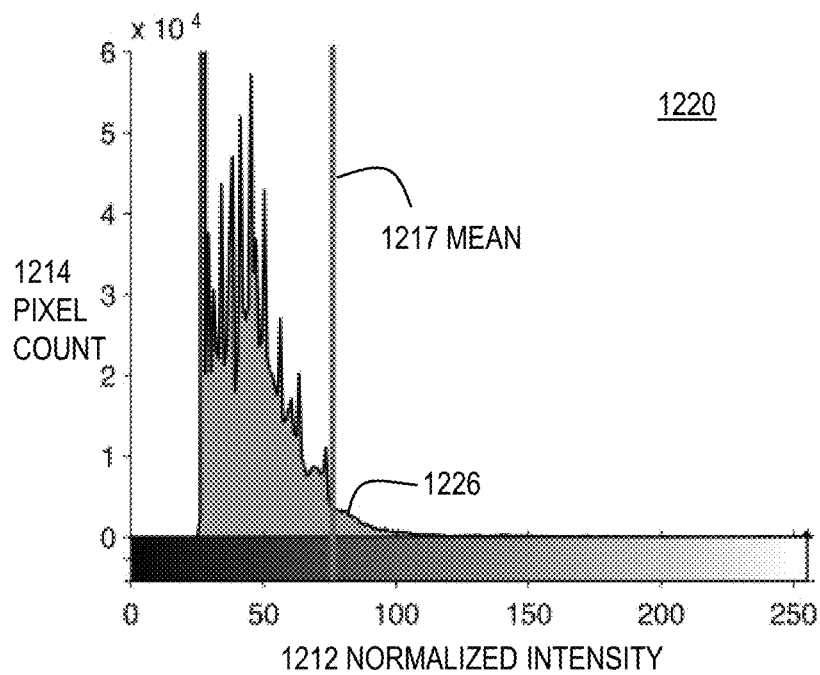

FIG. 12A and FIG. 12B are graphs 1210 and 1220 that illustrate example histograms 1216 and 1226, respectively, of pixel intensities for the images of FIG. 11A and FIG. 11B, respectively, according to some embodiments. The horizontal axis 1212 indicates normalized intensity, and the vertical axis indicates pixel count. Normalized intensity is relative to maximum intensity during normal breathing, e.g., in ROI of FIG. 11A and histogram 1210 of FIG. 12A. The mean 1217 of the distribution of the normal histogram 1216 is also plotted over the obstructed histogram 1226 for reference. In this embodiment, FIG. 12A has the corresponding peak to the far right. The threshold (mean) in the first image is applied to the second only to demonstrate that most pixels in FIG. 12B fall below the mean of the 12A. For purposes of classification, in the example embodiment, the image is considered obstructed (i.e., to depict an obstructed airway) only when ≥95% of the pixels fall below this mean. In some embodiments, this threshold is dynamically changed in a graphical user interface to assess sensitivity/false discovery rate.

Figure 13:
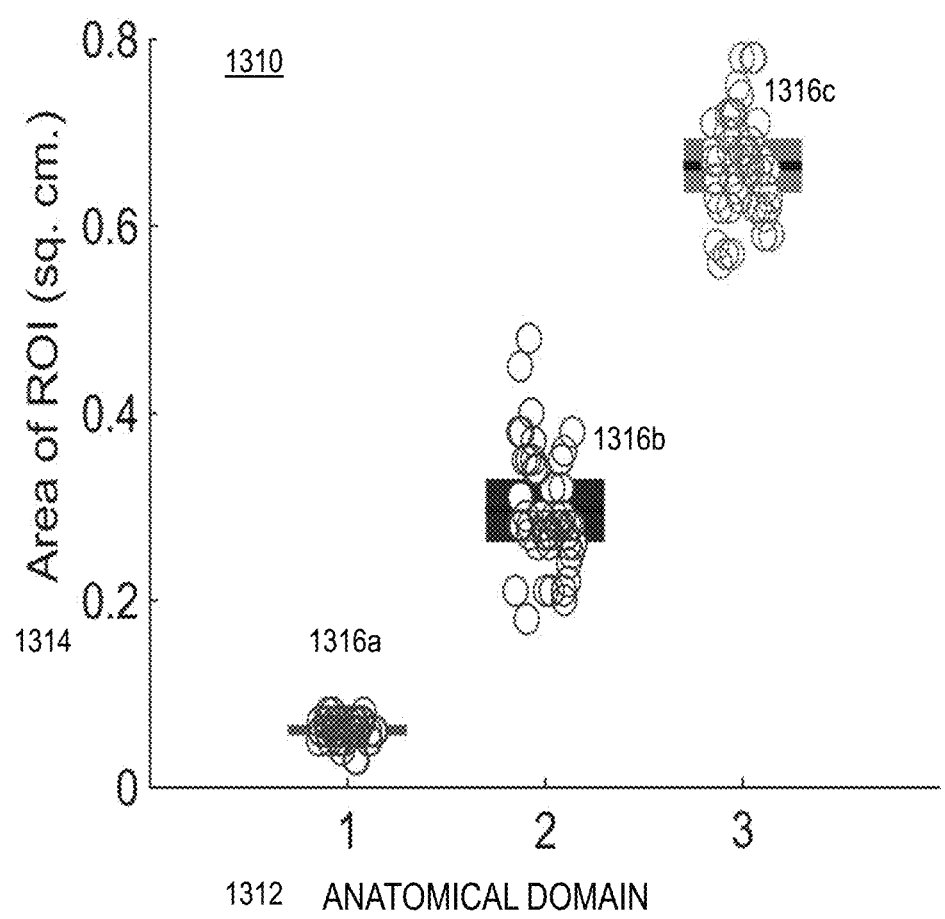
FIG. 13 is a graph that illustrates example dependence on the anatomical domain of the measured area of high intensity contiguous pixels in the region of interest, respectively, according to some embodiments.

Over 150 cross sectional images were obtained from each of four cadaver subjects. The method 500 of FIG. 5A, using the property of the total area of contiguous pixels that exceed the threshold in selected sets, was applied to each cadaver while the cadaver was maintained with an open airway to determine the total area in each ROI of contiguous pixels that exceed the threshold for selected sets. It was found that this area depended significantly on anatomical domain. FIG. 13 is a graph that illustrates example dependence on the anatomical domain of the measured area of high intensity contiguous pixels in the region of interest, respectively, according to some embodiments. The horizontal axis indicates anatomical domain, where 1 indicates the retropalatal domain, 2 indicates the retrolingual domain, and 3 indicates the hypopharyngeal domain. The vertical axis indicates the total measured area of selected sets of contiguous pixels that exceed the threshold of two standard deviations above the mean intensity in each ROI in square centimeters ($cm^2$). Points 1316a indicate that the areas per ROI are about 0.2 to about 0.1 $cm^2$ in the retropalatal domain, much less than the total areas per ROI of about 0.2 to about 0.5 $cm^2$ in the retrolingual domain indicated by points 1316b. Points 1316c indicate that the areas per ROI are about 0.55 to about 0.8 $cm^2$ in the hypopharyngeal domain, significantly more than the total areas per ROI in the retrolingual domain indicated by points 1316b. This is justification for separating these analyses by anatomical domain in some embodiments.

FIG. 14A through FIG. 14D are graphs that illustrates example dependence of the averaged measured area of high intensity contiguous pixels in a region of interest (ROI) for unobstructed and obstructed airways for four different subjects, according to some embodiments. The horizontal axis 1412 indicates whether the average was for an obstructed or unobstructed airway. The vertical axis 1414 indicates the total area of selected sets of contiguous high intensity pixels per ROI in square centimeters ($cm^2$). The different subjects are represented by different graphs 1410, 1420, 1430, 1440. For each subject, the range of areas is plotted for both unobstructed airways 1416, 1426, 1436 and 1446, respectively, and obstructed airways 1417, 1427, 1437 and 1447, respectively. The whiskers show±3 standard deviation (SD) and hence the far outliers are discarded. The box spans 25-75% interquartile range of the data. The notches correspond to the means of the data. As expected, the areas of high intensity contiguous pixels per ROI are significantly smaller for the obstructed airways than for the open airways.

FIG. 15A through FIG. 15D are graphs that illustrates example dependence of the individual measured area of high intensity contiguous pixels in a region of interest (ROI) for unobstructed and obstructed airways for four different subjects, according to some embodiments. The horizontal axis 1512 indicates the total area of selected sets of contiguous high intensity pixels per ROI in square centimeters ($cm^2$). The vertical axes 1514 indicate the fraction of 150 slices at or below that value. The different subjects are represented by different graphs 1510, 1520, 1530, 1540. For each subject, the cumulative distribution of areas is plotted for both unobstructed airways on traces 1516, 1526, 1536 and 1546, respectively, and for obstructed airways on traces 1517, 1527, 1537 and 1547, respectively. As expected, the areas of high intensity contiguous pixels per ROI is significantly smaller for the obstructed airways than for the open airways as each obstructed curve lies significantly below the unobstructed curve.

2.2 Curved 2-D Transducer Array Without Beamforming

Figure 16A:
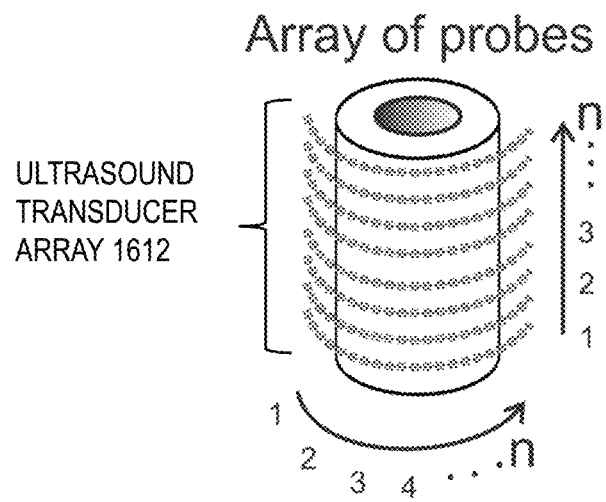
FIG. 16A is a block diagram that illustrates example 2D array of ultrasound transducers for simulations of an automated obstruction location method, according to some embodiments.

FIG. 16A is a block diagram that illustrates example 2D array 1612 of ultrasound transducers for simulations of an automated obstruction location method, according to some embodiments. The algorithm shown in FIG. 5 is applied to images obtained by an n x n array of transducers. Each transducer obtains signals from a scan line with a given spatial location (vertical and horizontal coordinates) along a beam. The symbol n refers to the number of the tagged transducer element.

Figure 16B:
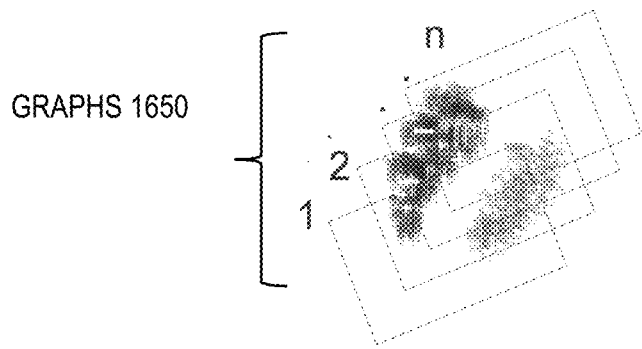
FIG. 16B is a set of graphs that illustrates example properties of each transducer measurement as a function of time during one respiratory cycle for two anatomical regions, according to some embodiments.
Figure 16C:
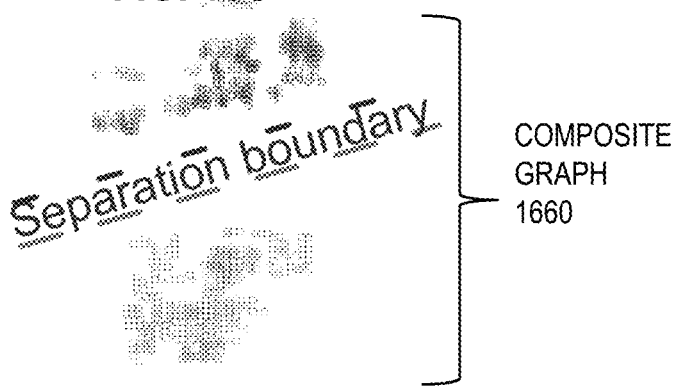
FIG. 16C is a graph that illustrates example properties of each transducer measurement as a function of time during one respiratory cycle, according to some embodiments.

FIG. 16B is a set of graphs 1650 that illustrates example properties of each transducer measurement as a function of time during one respiratory cycle for two anatomical regions, according to some embodiments. The ultrasound-based ROI information from the airway is separated by a mathematical classifier that is trained to identify the site of obstruction based on maximal variance of a set parameter (e.g. luminal diameter measured by ultrasound, where luminal diameter refers to the diameter of high intensity contiguous pixels in a ROI) associated with each respiratory cycle. Once this is identified, FIG. 16C is a graph 1660 that illustrates example properties of each transducer measurement as a function of time during one respiratory cycle, according to some embodiments. Planes of separation are drawn between distinct anatomic boundaries that may demonstrate different degrees of collapse when negative pressure is applied in the absence of air flow, as may be observed in obstructive sleep apnea.

Figure 17:
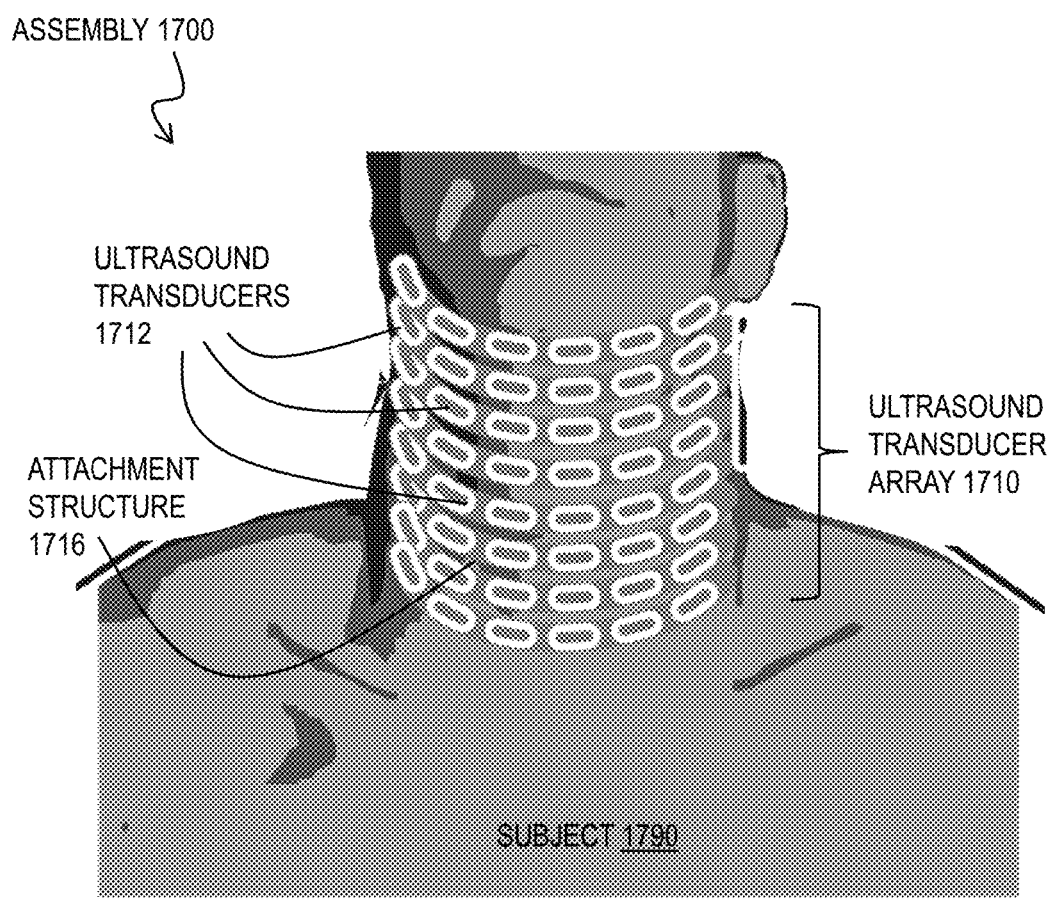
FIG. 17 is a block diagram that illustrates an example curved two dimensional array that follows a curvature of an attachment structure when the attachment structure is removably fitted around a neck of the subject, according to some embodiments.

FIG. 17 is a block diagram that illustrates an example curved two dimensional array 1710 that follows a curvature of an attachment structure 1716 when the attachment structure is removably fitted around a neck of the subject, according to some embodiments. The individual ultrasound transducers 1712 are affixed to the removable attachment structure 1716. Thus, FIG. 17 illustrates a circumferential scanner assembly 1700 that holds the transducers. In some embodiments, the assembly 1700 is held within an expandable, elasticated and tubular fabric (e.g. Dacron) with radial and linear reinforcements as attachment structure 1716. These reinforcements prevent the proximal-to-distal and lateral migration of the assembly 1700.

3.3 Curved 2D Transducer Array with Beamforming

Figure 18:
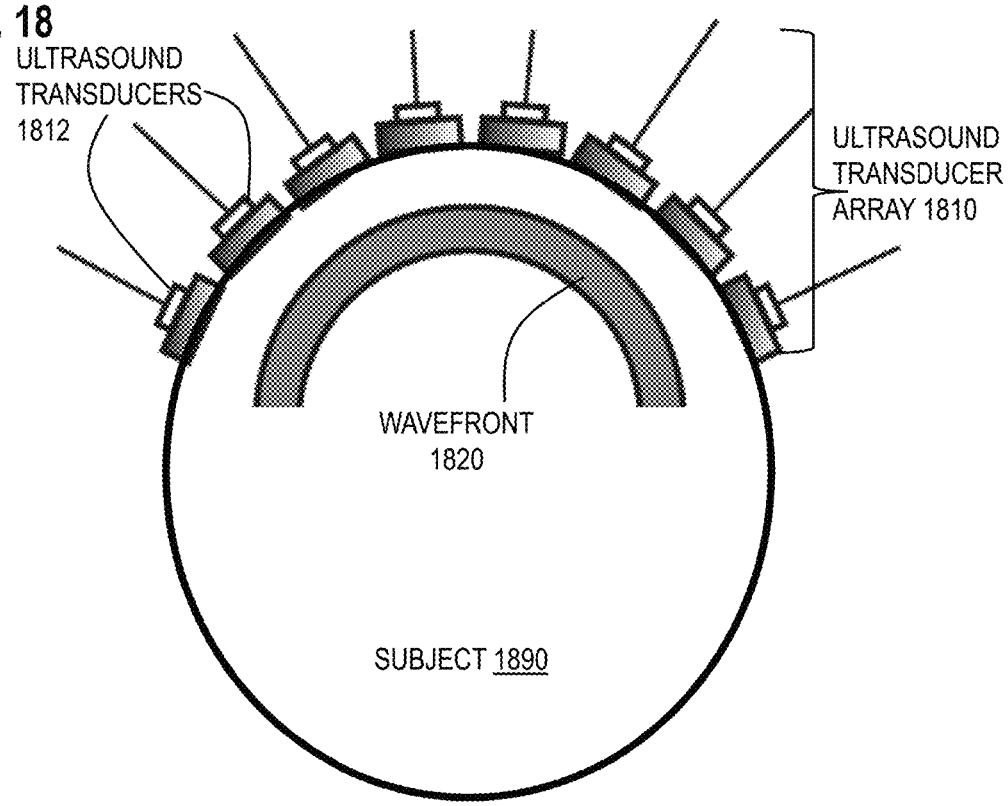
FIG. 18 is a block diagram that illustrates an example curved ultrasound wavefront determined by beamforming over a curved 1D array of transducers, according to some embodiments.

FIG. 18 is a block diagram that illustrates an example curved ultrasound wavefront 1820 determined by beamforming over a curved 1D array 1810 of transducers 1812, according to some embodiments. Thus, FIG. 18 illustrates application of a phased array probe in a 2-dimensional configuration, capable of generating multiple wavefront that can scan a large area of interest, and an arrangement of a phased array probe system circumferentially around a schematic of the human neck in which each individual probe is capable of generating its own wavefront in a subject 1890.

3.2 Alternative Transducer Shapes and Arrays

Figure 19A:
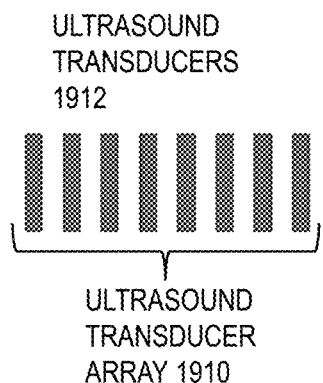
FIG. 19A through FIG. 19C are block diagrams that illustrate example transducer arrays, according to some embodiments.
Figure 19B:
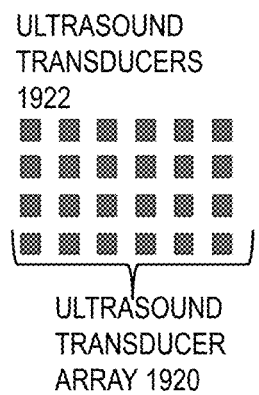
Figure 19C:
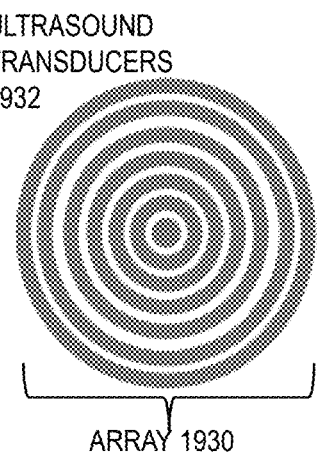

FIG. 19A through FIG. 19C are block diagrams that illustrate example transducer arrays, according to some embodiments. Such custom-fitting probe designs improve the resolution of the scanner. FIG. 19A depicts a linear 1D ultrasound transducer array 1910 made up of individual linear ultrasound transducers 1912. Such a linear array performing a 2D scan only may be the default mode for some embodiments. FIG. 19B depicts a 2D ultrasound transducer array 1920 made up of individual spot ultrasound transducers 1922. FIG. 19C depicts a 2D ultrasound transducer array 1930 made up of individual circular ultrasound transducers 1932. Such additional probe designs are anticipated to be useful for improving the spatial resolution of the scanner, minimizing the artifacts, or improving the signal-to-noise ratio (SNR), or some combination.

4. Computational Hardware Overview

Figure 20:
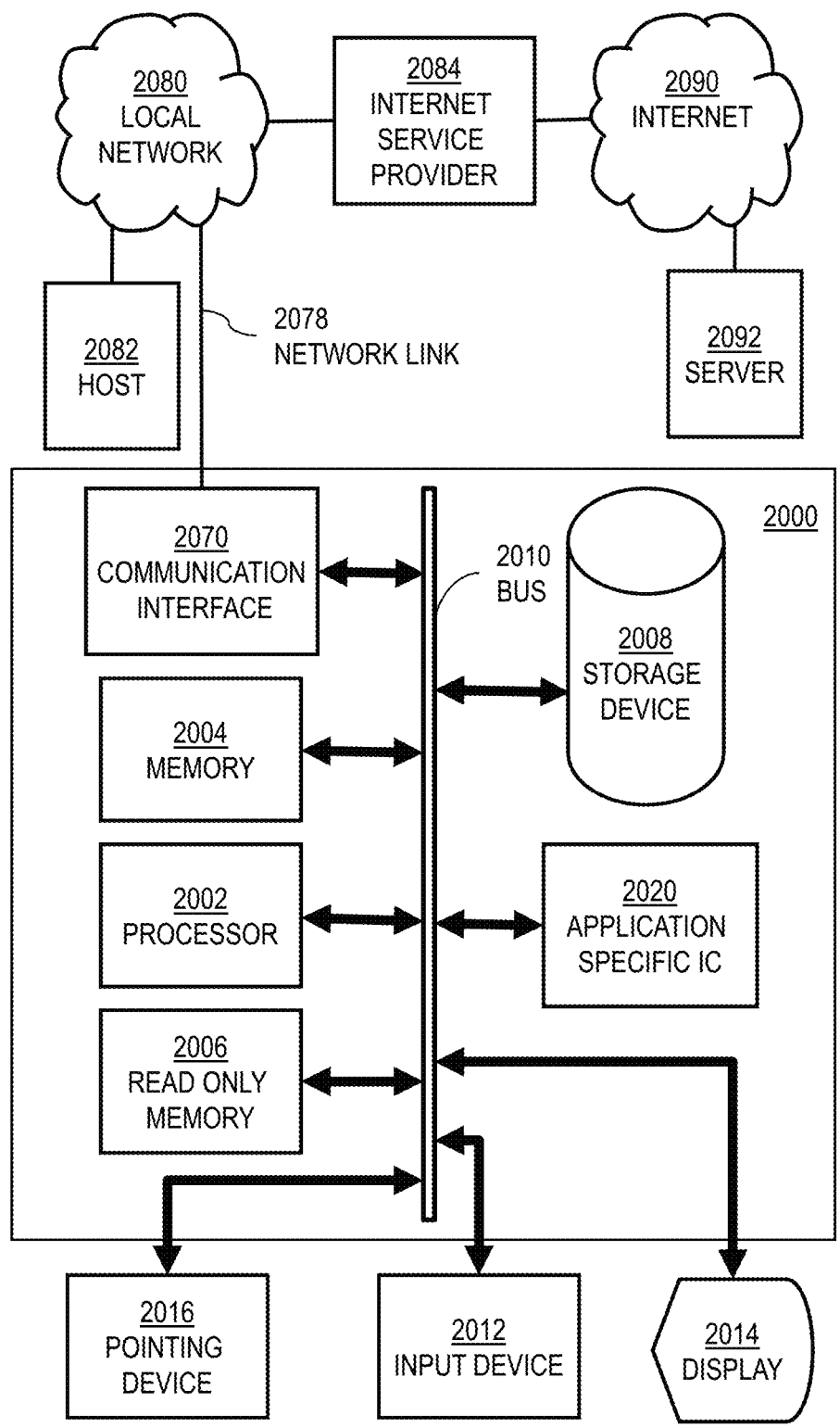
FIG. 20 is a block diagram that illustrates a computer system 2000 upon which an embodiment of the invention may be implemented.

FIG. 20 is a block diagram that illustrates a computer system 2000 upon which an embodiment of the invention may be implemented. Computer system 2000 includes a communication mechanism such as a bus 2010 for passing information between other internal and external components of the computer system 2000. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 2000, or a portion thereof, constitutes a means for performing one or more steps of one or more methods described herein.

A sequence of binary digits constitutes digital data that is used to represent a number or code for a character. A bus 2010 includes many parallel conductors of information so that information is transferred quickly among devices coupled to the bus 2010. One or more processors 2002 for processing information are coupled with the bus 2010. A processor 2002 performs a set of operations on information. The set of operations include bringing information in from the bus 2010 and placing information on the bus 2010. The set of operations also typically include comparing two or more units of information, shifting positions of units of information, and combining two or more units of information, such as by addition or multiplication. A sequence of operations to be executed by the processor 2002 constitutes computer instructions.

Computer system 2000 also includes a memory 2004 coupled to bus 2010. The memory 2004, such as a random access memory (RAM) or other dynamic storage device, stores information including computer instructions. Dynamic memory allows information stored therein to be changed by the computer system 2000. RAM allows a unit of information stored at a location called a memory address to be stored and retrieved independently of information at neighboring addresses. The memory 2004 is also used by the processor 2002 to store temporary values during execution of computer instructions. The computer system 2000 also includes a read only memory (ROM) 2006 or other static storage device coupled to the bus 2010 for storing static information, including instructions, that is not changed by the computer system 2000. Also coupled to bus 2010 is a non-volatile (persistent) storage device 2008, such as a magnetic disk or optical disk, for storing information, including instructions, that persists even when the computer system 2000 is turned off or otherwise loses power.

Information, including instructions, is provided to the bus 2010 for use by the processor from an external input device 2012, such as a keyboard containing alphanumeric keys operated by a human user, or a sensor. A sensor detects conditions in its vicinity and transforms those detections into signals compatible with the signals used to represent information in computer system 2000. Other external devices coupled to bus 2010, used primarily for interacting with humans, include a display device 2014, such as a cathode ray tube (CRT) or a liquid crystal display (LCD), for presenting images, and a pointing device 2016, such as a mouse or a trackball or cursor direction keys, for controlling a position of a small cursor image presented on the display 2014 and issuing commands associated with graphical elements presented on the display 2014.

In the illustrated embodiment, special purpose hardware, such as an application specific integrated circuit (IC) 2020, is coupled to bus 2010. The special purpose hardware is configured to perform operations not performed by processor 2002 quickly enough for special purposes. Examples of application specific ICs include graphics accelerator cards for generating images for display 2014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 2000 also includes one or more instances of a communications interface 2070 coupled to bus 2010. Communication interface 2070 provides a two-way communication coupling to a variety of external devices that operate with their own processors, such as printers, scanners and external disks. In general the coupling is with a network link 2078 that is connected to a local network 2080 to which a variety of external devices with their own processors are connected. For example, communication interface 2070 may be a parallel port or a serial port or a universal serial bus (USB) port on a personal computer. In some embodiments, communications interface 2070 is an integrated services digital network (ISDN) card or a digital subscriber line (DSL) card or a telephone modem that provides an information communication connection to a corresponding type of telephone line. In some embodiments, a communication interface 2070 is a cable modem that converts signals on bus 2010 into signals for a communication connection over a coaxial cable or into optical signals for a communication connection over a fiber optic cable. As another example, communications interface 2070 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 2070 sends and receives electrical, acoustic or electromagnetic signals, including infrared and optical signals, that carry information streams, such as digital data.

The term computer-readable medium is used herein to refer to any medium that participates in providing information to processor 2002, including instructions for execution. Such a medium may take many forms, including, but not limited to, non-volatile media, volatile media and transmission media. Non-volatile media include, for example, optical or magnetic disks, such as storage device 2008. Volatile media include, for example, dynamic memory 2004. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 2002, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 2002, except for carrier waves and other signals.

Logic encoded in one or more tangible media includes one or both of processor instructions on a computer-readable storage media and special purpose hardware, such as ASIC 2020.

Network link 2078 typically provides information communication through one or more networks to other devices that use or process the information. For example, network link 2078 may provide a connection through local network 2080 to a host computer 2082 or to equipment 2084 operated by an Internet Service Provider (ISP). ISP equipment 2084 in turn provides data communication services through the public, world-wide packet-switching communication network of networks now commonly referred to as the Internet 2090. A computer called a server 2092 connected to the Internet provides a service in response to information received over the Internet. For example, server 2092 provides information representing video data for presentation at display 2014.

The invention is related to the use of computer system 2000 for implementing the techniques described herein. According to one embodiment of the invention, those techniques are performed by computer system 2000 in response to processor 2002 executing one or more sequences of one or more instructions contained in memory 2004. Such instructions, also called software and program code, may be read into memory 2004 from another computer-readable medium such as storage device 2008. Execution of the sequences of instructions contained in memory 2004 causes processor 2002 to perform the method steps described herein. In alternative embodiments, hardware, such as application specific integrated circuit 2020, may be used in place of or in combination with software to implement the invention. Thus, embodiments of the invention are not limited to any specific combination of hardware and software.

The signals transmitted over network link 2078 and other networks through communications interface 2070, carry information to and from computer system 2000. Computer system 2000 can send and receive information, including program code, through the networks 2080, 2090 among others, through network link 2078 and communications interface 2070. In an example using the Internet 2090, a server 2092 transmits program code for a particular application, requested by a message sent from computer 2000, through Internet 2090, ISP equipment 2084, local network 2080 and communications interface 2070. The received code may be executed by processor 2002 as it is received, or may be stored in storage device 2008 or other non-volatile storage for later execution, or both. In this manner, computer system 2000 may obtain application program code in the form of a signal on a carrier wave.

Various forms of computer readable media may be involved in carrying one or more sequence of instructions or data or both to processor 2002 for execution. For example, instructions and data may initially be carried on a magnetic disk of a remote computer such as host 2082. The remote computer loads the instructions and data into its dynamic memory and sends the instructions and data over a telephone line using a modem. A modem local to the computer system 2000 receives the instructions and data on a telephone line and uses an infra-red transmitter to convert the instructions and data to a signal on an infra-red a carrier wave serving as the network link 2078. An infrared detector serving as communications interface 2070 receives the instructions and data carried in the infrared signal and places information representing the instructions and data onto bus 2010. Bus 2010 carries the information to memory 2004 from which processor 2002 retrieves and executes the instructions using some of the data sent with the instructions. The instructions and data received in memory 2004 may optionally be stored on storage device 2008, either before or after execution by the processor 2002.

Figure 21:
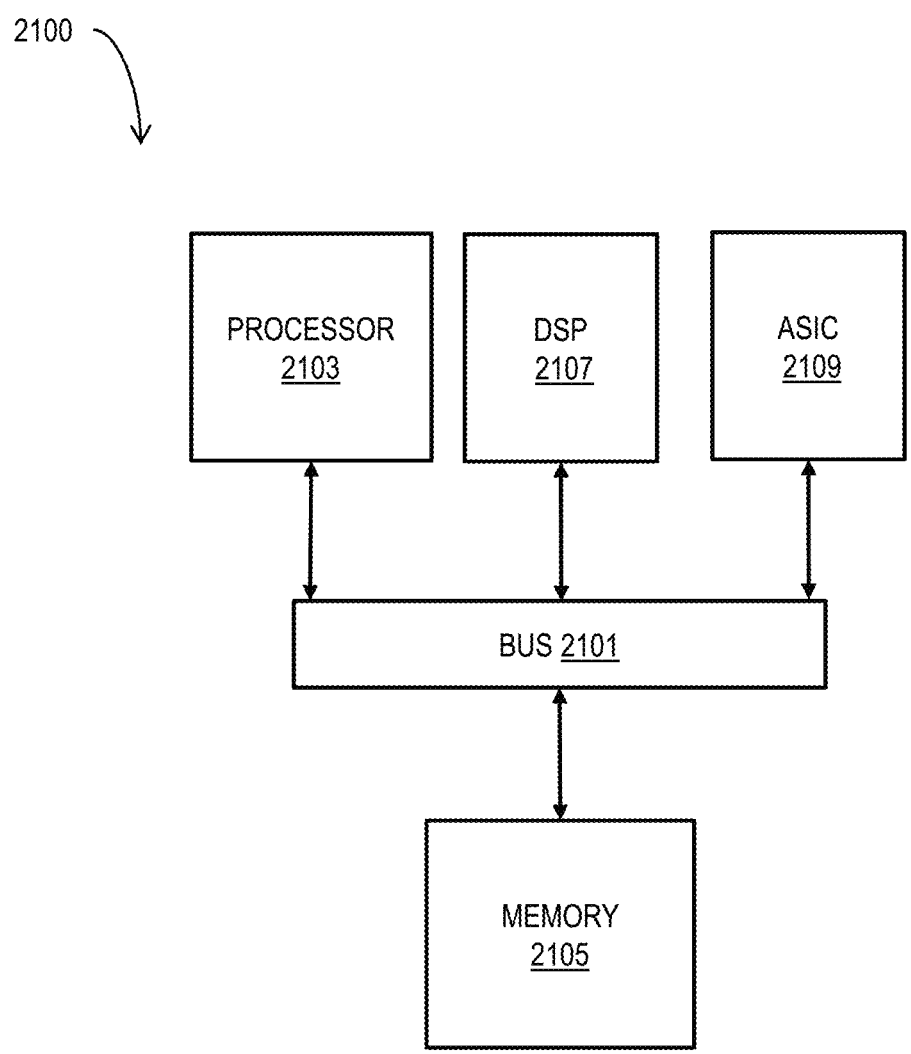
FIG. 21 illustrates a chip set 2100 upon which an embodiment of the invention may be implemented.

FIG. 21 illustrates a chip set 2100 upon which an embodiment of the invention may be implemented. Chip set 2100 is programmed to perform one or more steps of a method described herein and includes, for instance, the processor and memory components described with respect to FIG. 20 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 2100, or a portion thereof, constitutes a means for performing one or more steps of a method described herein.

In one embodiment, the chip set 2100 includes a communication mechanism such as a bus 2101 for passing information among the components of the chip set 2100. A processor 2103 has connectivity to the bus 2101 to execute instructions and process information stored in, for example, a memory 2105. The processor 2103 may include one or more processing cores with each core configured to perform independently. A multi-core processor enables multiprocessing within a single physical package. Examples of a multi-core processor include two, four, eight, or greater numbers of processing cores. Alternatively or in addition, the processor 2103 may include one or more microprocessors configured in tandem via the bus 2101 to enable independent execution of instructions, pipelining, and multithreading. The processor 2103 may also be accompanied with one or more specialized components to perform certain processing functions and tasks such as one or more digital signal processors (DSP) 2107, or one or more application-specific integrated circuits (ASIC) 2109. A DSP 2107 typically is configured to process real-world signals (e.g., sound) in real time independently of the processor 2103. Similarly, an ASIC 2109 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 2103 and accompanying components have connectivity to the memory 2105 via the bus 2101. The memory 2105 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 2105 also stores the data associated with or generated by the execution of one or more steps of the methods described herein.

5. Alternatives, Variations and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus a range from 0 to 10 includes the range 1 to 4 in some embodiments.

6. References

Bhattacharyya, N., Blake, S. P. & Fried, M. P. 2000. Assessment of the airway in obstructive sleep apnea syndrome with 3-dimensional airway computed tomography. Otolaryngology—Head and Neck Surgery 123: 444-449.

Chaban, R., Cole, P. & Hoffstein, V. 1988. Site of upper airway obstruction in patients with idiopathic obstructive sleep apnea. Laryngoscope 98: 641-647.

Clement, G., White, J. & Hynynen, K. 2000. Investigation of a large-area phased array for focused ultrasound surgery through the skull. Physics in Medicine and Biology 45, 1071.

Collop, N., Anderson, W. M., Boehlecke, B., Claman, D., Goldberg, R., Gottlieb, D. J., Hudgel, D., Sataia, M., & Schwab, R. 2007. Clinical guidelines for the use of unattended portable monitors in the diagnosis of obstructive sleep apnea in adult patients. J Clin Sleep Med 3: 737-747.

Crane, J. P., LeFevre, M. L., Winborn, R. C., Evans, J. K., Ewigman, B. G., Bain, R. P., Frigoletto, F. D., McNellis, D., & RADIUS Study Group. 1994. A randomized trial of prenatal ultrasonographic screening: impact on the detection, management, and outcome of anomalous fetuses. Am J Obstetrics and Gynecology 171: 392.

Croft, C. & Pringle, M. 1991. Sleep nasendoscopy: a technique of assessment in snoring and obstructive sleep apnoea. Clinical Otolaryngology & Allied Sciences 16: 504-509.

Deberry-Borowiecki, B., Kukwa, A. & Blanks, R. H. 1988. Cephalometric analysis for diagnosis and treatment of obstructive sleep apnea. Laryngoscope 98: 226-234.

Ezri, T., Gewürtz, G., Sessler, D. I., Medalion, B., Szmuk, P., Hagberg, C., & Susmallian, S. 2003. Prediction of difficult laryngoscopy in obese patients by ultrasound quantification of anterior neck soft tissue. Anaesthesia 58: 1111-1114.

Findley, L., Barth J. T., Powers D. C., Wilhoit S. C., Boyd D. G. & Suratt P. M. 1986. Cognitive impairment in patients with obstructive sleep apnea and associated hypoxemia. Chest 90(5): 686-690.

Flemons, W. W. 2002. Obstructive sleep apnea. New England Journal of Medicine 347: 498-504.

Gardin, J. M., FASE, M. G.-H., Jaff, M. & Mohler, E. 2006. Clinical application of noninvasive vascular ultrasound in cardiovascular risk stratification: a report from the American Society of Echocardiography and the Society of Vascular Medicine and Biology. J Am Soc Echocardiogr 19: 943-954.

Girard, E. E. 2003. Automated Detection of Obstructive Sleep Apnea Using Ultrasound Imaging. Charlottesville, Va.: University of Virginia.

Guilleminault, C., Connolly, S. J. & Winkle, R. A. 1983. Cardiac arrhythmia and conduction disturbances during sleep in 400 patients with sleep apnea syndrome. American J Cardio 52: 490-494.

Guilleminault, C., Riley, R. & Powell, N. 1984. Obstructive sleep apnea and abnormal cephalometric measurements. Implications for treatment. Chest 86: 793-794.

Hamers, R., Bruining, N., Knook, M., Sabate, M. & Roelandt, J. 2001. A Novel Approach to Quantitative Analysis of Intra Vascular Ultrasound Images. In: Computers in Cardiology. IEEE: 589-592.

Hoskins, P. R., Martin, K. & Thrush, A. 2010. Diagnostic ultrasound: physics and equipment. Cambridge, U.K.: Cambridge University Press.

Hudgel, D. W. 1986. Variable site of airway narrowing among obstructive sleep apnea patients. J Applied Physiology 61: 1403-1409.

Hung, J., Whitford, E., Hillman, D. & Parsons, R. Association of sleep apnoea with myocardial infarction in men. 1990. Lancet 336: 261-264.

Johns, M. W. 1993. Daytime sleepiness, snoring, and obstructive sleep apnea: The Epworth Sleepiness Scale. Chest 103(1): 30-36.

Kajekar, P., Mendonca, C. & Gaur, V. 2010. Role of Ultrasound in Airway Assessment and Management. International J Ultrasound & Applied Technologies in Perioperative Care 1: 97-100.

Kuratli, C. & Huang, Q. 2000. A CMOS ultrasound rangefinder microsystem. IEEE Journal of Solid-State Circuits 35: 2005-2017.

Marin, J. M., Carrizo, S. J., Vicente, E. & Agusti, A. G. 2005. Long-term cardiovascular outcomes in men with obstructive sleep apnoea-hypopnoea with or without treatment with continuous positive airway pressure: an observational study. Lancet 365: 1046-1053.

McNay, M. B. & Fleming, J. E. 1999. Forty years of obstetric ultrasound 1957-1997: From A-scope to three dimensions. Ultrasound in Medicine and Biology 25: 3-56.

Morrison, D., Launois, S. H., Isono, S., Feroah, T. R., Whitelaw, W. A., & Remmers, J. E. 1993. Pharyngeal narrowing and closing pressures in patients with obstructive sleep apnea. American J Respiratory and Critical Care Medicine 148(3): 606-611.

Muthukumaran, S., Yang, K., Seuren, A., Kentish, S., Ashokkumar, M., Stevens, G. W., & Grieser, F. 2004. The use of ultrasonic cleaning for ultrafiltration membranes in the dairy industry. Separation and purification technology 39, 99-107.

Pepin, J., Ferretti, G., Veale, D., Romand, P., Coulomb, M., Brambilla, C., & Lévy, P. A. 1992. Somnofluoroscopy, computed tomography, and cephalometry in the assessment of the airway in obstructive sleep apnoea. Thorax 47(3): 1506-156.

Riley, R., Guilleminault, C., Powell, N. & Simmons, F. 1985. Palatopharyngoplasty failure, cephalometric roentgenograms, and obstructive sleep apnea. Otolaryngology—Head and Neck Surgery 93: 240.

Riley, R. W., Powell, N. B. & Guilleminault, C. 1993. Obstructive sleep apnea syndrome: a review of 306 consecutively treated surgical patients. Otolaryngology—Head and Neck Surgery 108: 117.

Rodenstein, D., Dooms, G., Thomas, Y., Liistro, G., Stanescu, D. C., Culée, C., & Aubert-Tulkens, G. 1990. Pharyngeal shape and dimensions in healthy subjects, snorers, and patients with obstructive sleep apnoea. Thorax 45(10): 722-727.

Romero, R. Routine obstetric ultrasound. 2003. Ultrasound in Obstetrics & Gynecology 3: 303-307.

Ruecroft, G., Hipkiss, D., Ly, T., Maxted, N. & Cains, P. W. 2005. Sonocrystallization: the use of ultrasound for improved industrial crystallization. Organic process research & development 9: 923-932.

Schwab, R. J., Pasirstein, M., Pierson, R., Mackley, A., Hachadoorian, R., Arens, R., Maislin, G., & Pack, A. I. 2003. Identification of upper airway anatomic risk factors for obstructive sleep apnea with volumetric magnetic resonance imaging. American J Respiratory and Critical Care Medicine 168(5): 522-530.

Shamsuzzaman, A. S., Gersh, B. J. & Somers, V. K. 2003. Obstructive sleep apnea. JAMA: the journal of the American Medical Association 290: 1906-1914.

Shelton, K. E., Woodson, H., Gay, S. & Suratt, P. M. 1993. Pharyngeal fat in obstructive sleep apnea. American Journal of Respiratory and Critical Care Medicine 148: 462-466.

Shepard, J. W. & Thawley, S. E. 1990. Localization of upper airway collapse during sleep in patients with obstructive sleep apnea. American Journal of Respiratory and Critical Care Medicine 141: 1350-1355.

Siegel, H., Sonies, B.C., Graham, B., McCutchen, C., Hunter, K., Vega—Bermudez, F., & Sato, S. 2000. Obstructive sleep apnea: A study by simultaneous polysomnography and ultrasonic imaging. Neurology 54: 1872-1872.

Silk, M. G. 1984. Ultrasonic transducers for nondestructive testing. London: Taylor & Francis.

Smith, S., Trahey, G. & Von Ramm, O. 1986. Phased array ultrasound imaging through planar tissue layers. Ultrasound in Medicine & Biology 12: 229-243.

Strollo Jr, P. J. & Rogers, R. M. 1996. Obstructive sleep apnea. New England Journal of Medicine 334: 99-104.

Teran-Santos, J., Jimenez-Gomez, A. & Cordero-Guevara, J. 1999. The association between sleep apnea and the risk of traffic accidents. New England J Med 340: 847-851.

Veasey, S. C., Guilleminault, C., Strohl, K. P., Sanders, M. H., Ballard, R. D., & Magalang, U. J. 2006. Medical therapy for obstructive sleep apnea: a review by the Medical Therapy for Obstructive Sleep Apnea Task Force of the Standards of Practice Committee of the American Academy of Sleep Medicine. Sleep 29(8): 1036.

What is claimed is:

1. A method comprising:
   placing an ultrasound transducer array such that the ultrasound transducer array is adjacent to a neck of a subject, wherein the transducer array is configured, upon receipt of a signal, to obtain first data that supports a plurality of ultrasound images representing a corresponding plurality of cross sections of an airway in the neck of the subject;
   receiving automatically on a processor second data from an apnea event sensor set configured to collect automatically the second data, wherein the second data is sensitive to an apnea event in the subject and the apnea event sensor does not provide an ultrasound image;
   automatically detecting on the processor an apnea event based on the second data; and,
   in response to detecting the apnea event,
      automatically sending, to the ultrasound transducer array, the signal that causes the ultrasound transducer array to obtain the first data, and
      automatically causing image data based on the first data to be stored in a computer-readable medium.

2. A method as recited in claim 1, further comprising automatically determining a location of an obstruction in an airway of the subject based on the first data.

3. A method as recited in claim 1, wherein the apnea sensor set includes one or more sensors from a group comprising a blood oxygen saturation sensor and a chest movement sensor and a microphone.

4. A method as recited in claim 1, wherein the ultrasound transducer array is removably attached to the subject by an attachment structure.

5. A method as recited in claim 1, wherein the ultrasound transducer array comprises a rotating one dimensional array.

6. A method as recited in claim 1, wherein the ultrasound transducer array comprises a two dimensional array.

7. A method as recited in claim 1, wherein the ultrasound transducer array comprises a curved two dimensional array that follows a curvature of an attachment structure when the attachment structure is removably fitted around a neck of the subject.

8. A computer-readable medium encoded with one or more sequences of instructions, wherein execution of the one or more sequences of instructions by one or more processors causes the one or more processors to perform the steps of:
- establishing communications with an ultrasound transducer array adjacent to a neck of a subject, wherein the transducer array is configured, upon receipt of a signal, to obtain first data that supports a plurality of ultrasound images representing a corresponding plurality of cross sections of an airway of the subject;
- establishing communications with an apnea event sensor set configured to collect automatically second data sensitive to an apnea event in the subject, wherein the apnea event sensor does not provide an ultrasound image;
- receiving the second data;
- detecting an apnea event based on the second data; and
- in response to detecting the apnea event,
  - sending, to the ultrasound transducer array, the signal that causes the ultrasound transducer array to obtain the first data, and
  - storing image data based on the first data in a second computer-readable medium.

9. A system comprising:
- an ultrasound transducer array configured, when disposed adjacent to a neck of a subject, to obtain first data upon receipt of a signal, wherein the first data supports a plurality of ultrasound images representing a corresponding plurality of cross sections of an airway of the subject;
- an apnea event sensor set configured to collect automatically second data sensitive to an apnea event in the subject, wherein the apnea event sensor does not provide an ultrasound image;
- at least one processor; and
- at least one computer-readable medium encoded with one or more sequences of instructions,
  - the at least one memory and the one or more sequences of instructions configured to, with
  - the at least one processor, cause the system to perform at least the following,
    - establish communications with the ultrasound transducer array;
    - establish communications with the apnea event sensor set;
    - receive the second data;
    - detect an apnea event based on the second data; and
    - in response to detecting the apnea event,
      - cause the signal that causes the ultrasound transducer array to obtain the first data to be sent to the ultrasound transducer array, and
      - cause image data based on the first data to be stored in a second computer-readable medium.

10. A method comprising:
- automatically receiving a first plurality of ultrasound images representing a corresponding plurality of two-dimensional cross sections of an airway in a neck of a subject obtained by an ultrasound transducer array directed toward the subject when the subject has an open airway;
- automatically associating each image in the first plurality of images with a corresponding subset of transducers in the ultrasound transducer array and a location of the corresponding two-dimensional cross section in the subject;
- determining a two-dimensional region of interest comprising a subset of pixels of each image of the first plurality of ultrasound images, wherein each region of interest encompasses the open airway for each corresponding two-dimensional cross section;
- automatically determining a first value of a statistic of pixel intensities for each region of interest;
- automatically receiving a second plurality of ultrasound images representing the corresponding plurality of two-dimensional cross sections of the airway in the neck of the subject obtained by the ultrasound transducer array directed toward the subject when the subject has an obstructive sleep apnea;
- automatically determining a second value of the statistic of pixel intensities for each subset of pixels in the second plurality of images that correspond to each region of interest of each image of the first plurality of ultrasound images;
- automatically determining whether the second value is significantly different from the first value for region of interest associated with a particular subset of transducers;
- if it is determined that the second value is significantly different, then automatically determining that the region of interest associated with the particular subset of transducers corresponds to a location of an obstruction in the subject during the obstructive sleep apnea event; and
- directing treatment of the subject based on the location of the obstruction.

11. A method as recited in claim 10, wherein the statistic is an area of contiguous pixels having an intensity above a threshold intensity value in the corresponding region of interest.

12. A method as recited in claim 10, wherein the contiguous pixels above the threshold value have an lateral extent greater than about two centimeters.

13. A method as recited in claim 10, wherein the threshold intensity value is at least one standard deviation above a mean intensity value for the corresponding region of interest in the first plurality of ultrasound images.

14. A method as recited in claim 13, wherein the threshold intensity value is at about three standard deviations above the mean intensity value.

15. A computer-readable medium encoded with one or more sequences of instructions, wherein execution of the one or more sequences of instructions by one or more processors causes the one or more processors to perform the steps of:
- receiving a first plurality of ultrasound images representing a corresponding plurality of two-dimensional cross sections of an airway in a neck of a subject obtained by an ultrasound transducer array directed toward the subject when the subject has an open airway;
- associating each image in the first plurality of images with a corresponding subset of transducers in the ultrasound transducer array and a location of the corresponding two-dimensional cross section in the subject;

determining a two-dimensional region of interest comprising a subset of pixels of each image of the first plurality of ultrasound images, wherein each region of interest encompasses the open airway for each corresponding two-dimensional cross section;

determining a first value of a statistic of pixel intensities for each region of interest;

receiving a second plurality of ultrasound images representing the corresponding plurality of two-dimensional cross sections of the airway in the neck of the subject obtained by the ultrasound transducer array directed toward the subject when the subject has an obstructive sleep apnea event;

determining a second value of the statistic of pixel intensities for each subset of pixels in the second plurality of images that correspond to each region of interest of each image of the first plurality of ultrasound images;

determining whether the second value is significantly different from the first value for region of interest associated with a particular subset of transducers;

if it is determined that the second value is significantly different, then determining that the region of interest associated with the particular subset of transducers corresponds to a location of an obstruction in the subject during the obstructive sleep apnea event; and present or store data indicating the location of the obstruction.

16. A system comprising:

at least one processor; and at least one computer-readable medium encoded with one or more sequences of instructions, the at least one memory and the one or more sequences of instructions configured to, with the at least one processor, cause the system to perform at least the following, receive a first plurality of ultrasound images representing a corresponding plurality of two-dimensional cross sections of an airway in a neck of a subject obtained by an ultrasound transducer array directed toward the subject when the subject has an open airway;

associate each image in the first plurality of images with a corresponding subset of transducers in the ultrasound transducer array and a location of the corresponding two-dimensional cross section in the subject;

determine a two-dimensional region of interest comprising a subset of pixels of each image of the first plurality of ultrasound images, wherein each region of interest encompasses the open airway for each corresponding two-dimensional cross section;

determine a first value of a statistic of pixel intensities for each region of interest;

receive a second plurality of ultrasound images representing the corresponding plurality of two-dimensional cross sections of the airway in the neck of the subject obtained by the ultrasound transducer array directed toward the subject when the subject has an obstructive sleep apnea event;

determine a second value of the statistic of pixel intensities for each subset of pixels in the second plurality of images that correspond to each region of interest of each image of the first plurality of ultrasound images;

determine whether the second value is significantly different from the first value for a particular region of interest associated with a corresponding particular subset of transducers;

if it is determined that the second value is significantly different, then determine that the particular region of interest associated with the particular subset of transducers corresponds to a location of an obstruction in the subject during the obstructive sleep apnea event; and present or store data indicating the location of the obstruction.

* * * * *